US009702839B2

(12) United States Patent
Ghaffari et al.

(10) Patent No.: US 9,702,839 B2
(45) Date of Patent: Jul. 11, 2017

(54) INTEGRATED DEVICES TO FACILITATE QUANTITATIVE ASSAYS AND DIAGNOSTICS

(75) Inventors: Roozbeh Ghaffari, Cambridge, MA (US); Stephen P. Lee, Cambridge, MA (US); Bassel De Graff, San Juan, PR (US)

(73) Assignee: MC10, Inc., Lexington, MA (US)

( * ) Notice: Subject to any disclaimer, the term of this patent is extended or adjusted under 35 U.S.C. 154(b) by 790 days.

(21) Appl. No.: 14/004,408

(22) PCT Filed: Mar. 9, 2012

(86) PCT No.: PCT/US2012/028590
§ 371 (c)(1),
(2), (4) Date: Sep. 10, 2013

(87) PCT Pub. No.: WO2012/125494
PCT Pub. Date: Sep. 20, 2012

(65) Prior Publication Data
US 2014/0001058 A1  Jan. 2, 2014

Related U.S. Application Data

(60) Provisional application No. 61/451,943, filed on Mar. 11, 2011.

(51) Int. Cl.
*G01N 27/327* (2006.01)
*G01N 27/02* (2006.01)
(Continued)

(52) U.S. Cl.
CPC ........ *G01N 27/02* (2013.01); *B01L 3/502707* (2013.01); *G01N 21/78* (2013.01);
(Continued)

(58) Field of Classification Search
CPC ............ G01N 27/403; G01N 27/3272; G01N 27/416; G01N 27/76; G01N 21/66
See application file for complete search history.

(56) References Cited

U.S. PATENT DOCUMENTS 3,716,861 A   2/1973   Root
3,805,427 A   4/1974   Epstein
(Continued)

FOREIGN PATENT DOCUMENTS

WO   WO 2005/122285 A2   12/2005
WO   WO 2008/030960 A2    3/2008
(Continued)

OTHER PUBLICATIONS

Grieshaber et al., "Electrochemical Biosensors—Sensor Principles and Architectures," Sensors 2008, 8, 1400-1458.*
(Continued)

*Primary Examiner* — Alexander Noguerola
(74) *Attorney, Agent, or Firm* — Nixon Peabody LLP; David F. Crosby

(57) ABSTRACT

Devices are described for providing quantitative information relating to a sample. Example devices include a flexible substrate, a sample receiver at least partially formed in or disposed on the flexible substrate, electronic circuitry and at least one indicator electrically coupled to the electronic circuitry. The flexible substrate includes at least one paper-based portion, at least one elastomeric portion, or at least one plastic portion. The electronic circuitry and the at least one indicator are at least partially formed in or disposed on the flexible substrate. The electronic circuitry generates an analysis result based on an output signal from the sample or a derivative of the sample. The at least one indicator
(Continued)

provides an indication of the quantitative information relating to the sample based at least in part on the at least one analysis result.

12 Claims, 30 Drawing Sheets

(51) Int. Cl.
  *G01N 21/78* (2006.01)
  *B01L 3/00* (2006.01)
  *G01N 21/84* (2006.01)
  *G01N 21/66* (2006.01)

(52) U.S. Cl.
  CPC ....... *G01N 21/8483* (2013.01); *G01N 27/327* (2013.01); *B01L 2200/12* (2013.01); *B01L 2300/0645* (2013.01); *B01L 2300/0816* (2013.01); *B01L 2300/0864* (2013.01); *B01L 2300/0874* (2013.01); *B01L 2300/0887* (2013.01); *B01L 2300/123* (2013.01); *B01L 2300/126* (2013.01); *B01L 2400/0406* (2013.01); *G01N 21/66* (2013.01)

(56) References Cited

U.S. PATENT DOCUMENTS

| | | | |
|---|---|---|---|
| 5,580,794 A | 12/1996 | Allen | |
| 5,817,008 A | 10/1998 | Rafert et al. | |
| 5,837,546 A | 11/1998 | Allen | |
| 5,907,477 A | 5/1999 | Tuttle et al. | |
| 5,968,839 A | 10/1999 | Blatt | |
| 6,009,632 A | 1/2000 | Douglas | |
| 6,063,046 A | 5/2000 | Allum | |
| 6,309,351 B1 | 10/2001 | Kurnik | |
| 6,322,963 B1 | 11/2001 | Bauer | |
| 6,403,944 B1 | 6/2002 | Mackenzie | |
| 6,784,844 B1 | 8/2004 | Boakes et al. | |
| 7,265,298 B2 | 9/2007 | Maghribi | |
| 7,302,751 B2 | 12/2007 | Hamburgen | |
| 7,337,012 B2 | 2/2008 | Maghribi | |
| 7,407,570 B2* | 8/2008 | Prince | G01N 33/48785 204/416 |
| 7,487,587 B2 | 2/2009 | Vanfleteren | |
| 7,491,892 B2 | 2/2009 | Wagner | |
| 7,521,292 B2 | 4/2009 | Rogers | |
| 7,557,367 B2 | 7/2009 | Rodgers | |
| 7,618,260 B2 | 11/2009 | Daniel et al. | |
| 7,622,367 B1 | 11/2009 | Nuzzo | |
| 7,759,167 B2 | 7/2010 | Vanfleteren | |
| 7,796,266 B2* | 9/2010 | Cohen | G01N 33/521 356/244 |
| 7,960,246 B2 | 6/2011 | Flamand | |
| 7,982,296 B2 | 7/2011 | Nuzzo | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rodgers | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rogers | |
| 8,664,699 B2 | 3/2014 | Nuzzo | |
| 8,679,888 B2 | 3/2014 | Rodgers | |
| 8,729,524 B2 | 5/2014 | Rodgers | |
| 8,754,396 B2 | 6/2014 | Rogers | |
| 8,865,489 B2 | 10/2014 | Rodgers | |
| 8,886,334 B2 | 11/2014 | Ghaffari | |
| 8,905,772 B2 | 12/2014 | Rodgers | |
| 9,012,784 B2 | 4/2015 | Arora | |
| 2002/0094701 A1 | 7/2002 | Biegelsen et al. | |
| 2002/0113739 A1 | 8/2002 | Howard | |
| 2003/0214408 A1 | 11/2003 | Grajales | |
| 2004/0243204 A1 | 12/2004 | Maghribi | |
| 2005/0037511 A1 | 2/2005 | Sharrock | |
| 2005/0072670 A1* | 4/2005 | Hasegawa | C12Q 1/001 204/403.01 |
| 2005/0096513 A1 | 5/2005 | Ozguz | |
| 2005/0136501 A1 | 6/2005 | Kuriger | |
| 2006/0038182 A1 | 2/2006 | Rodgers | |
| 2006/0264767 A1 | 11/2006 | Shennib | |
| 2006/0286785 A1 | 12/2006 | Rogers | |
| 2007/0122819 A1 | 5/2007 | Wu | |
| 2007/0123756 A1 | 5/2007 | Kitajima et al. | |
| 2008/0046080 A1 | 2/2008 | Vanden Bulcke | |
| 2008/0139894 A1 | 6/2008 | Szydlo-Moore et al. | |
| 2008/0157235 A1 | 7/2008 | Rodgers | |
| 2008/0204021 A1 | 8/2008 | Leussler et al. | |
| 2008/0259576 A1 | 10/2008 | Johnson et al. | |
| 2009/0000377 A1 | 1/2009 | Shipps et al. | |
| 2009/0048556 A1 | 2/2009 | Durand | |
| 2009/0107704 A1 | 4/2009 | Vanfleteren | |
| 2009/0261828 A1 | 10/2009 | Nordmeyer-Massner | |
| 2009/0294803 A1 | 12/2009 | Nuzzo | |
| 2009/0322480 A1 | 12/2009 | Benedict et al. | |
| 2010/0002402 A1 | 1/2010 | Rodgers | |
| 2010/0059863 A1 | 3/2010 | Rogers | |
| 2010/0072577 A1 | 3/2010 | Nuzzo | |
| 2010/0087782 A1 | 4/2010 | Ghaffari | |
| 2010/0090824 A1 | 4/2010 | Rowell et al. | |
| 2010/0116526 A1 | 5/2010 | Arora | |
| 2010/0178722 A1 | 7/2010 | De Graff | |
| 2010/0245011 A1 | 9/2010 | Chatzopoulos et al. | |
| 2010/0271191 A1 | 10/2010 | De Graff | |
| 2010/0298895 A1 | 11/2010 | Ghaffari | |
| 2010/0317132 A1 | 12/2010 | Rodgers | |
| 2010/0321161 A1 | 12/2010 | Isabell | |
| 2011/0034912 A1 | 2/2011 | De Graff | |
| 2011/0054583 A1 | 3/2011 | Litt | |
| 2011/0101789 A1 | 5/2011 | Salter et al. | |
| 2011/0121822 A1 | 5/2011 | Parsche | |
| 2011/0140897 A1 | 6/2011 | Purks et al. | |
| 2011/0184320 A1 | 7/2011 | Shipps | |
| 2011/0215931 A1 | 9/2011 | Callsen | |
| 2011/0218756 A1 | 9/2011 | Callsen | |
| 2011/0218757 A1 | 9/2011 | Callsen | |
| 2011/0220890 A1 | 9/2011 | Nuzzo | |
| 2011/0277813 A1 | 11/2011 | Rodgers | |
| 2012/0016258 A1 | 1/2012 | Webster et al. | |
| 2012/0051005 A1 | 3/2012 | Vanfleteren | |
| 2012/0052268 A1 | 3/2012 | Axisa | |
| 2012/0065937 A1 | 3/2012 | De Graff | |
| 2012/0087216 A1 | 4/2012 | Keung et al. | |
| 2012/0092178 A1 | 4/2012 | Callsen | |
| 2012/0092222 A1 | 4/2012 | Kato et al. | |
| 2012/0157804 A1 | 6/2012 | Rodgers | |
| 2012/0172697 A1 | 7/2012 | Urman | |
| 2012/0226130 A1 | 9/2012 | De Graff | |
| 2012/0244848 A1 | 9/2012 | Ghaffari | |
| 2012/0256308 A1 | 10/2012 | Helin | |
| 2012/0316455 A1 | 12/2012 | Rahman et al. | |
| 2012/0327608 A1 | 12/2012 | Rodgers | |
| 2013/0041235 A1 | 2/2013 | Rodgers | |
| 2013/0099358 A1 | 4/2013 | Elolampi | |
| 2013/0100618 A1 | 4/2013 | Rogers | |
| 2013/0118255 A1 | 5/2013 | Callsen | |
| 2013/0150693 A1 | 6/2013 | D'angelo | |
| 2013/0185003 A1 | 7/2013 | Carbeck | |
| 2013/0192356 A1 | 8/2013 | De Graff | |
| 2013/0200268 A1 | 8/2013 | Rafferty | |
| 2013/0211761 A1 | 8/2013 | Brandsma et al. | |
| 2013/0225965 A1 | 8/2013 | Ghaffari | |
| 2013/0245388 A1 | 9/2013 | Rafferty | |
| 2013/0274562 A1 | 10/2013 | Ghaffari | |
| 2013/0313713 A1 | 11/2013 | Arora | |
| 2013/0316442 A1 | 11/2013 | Meurville et al. | |
| 2013/0316487 A1 | 11/2013 | De Graff | |
| 2013/0320503 A1 | 12/2013 | Nuzzo | |
| 2014/0001058 A1 | 1/2014 | Ghaffari | |
| 2014/0012160 A1 | 1/2014 | Ghaffari | |
| 2014/0012242 A1 | 1/2014 | Lee | |

(56) References Cited

U.S. PATENT DOCUMENTS

| | | |
|---|---|---|
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |

FOREIGN PATENT DOCUMENTS

| | | |
|---|---|---|
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |

OTHER PUBLICATIONS

Nie et al., "Electrochemical sensing in paper-based microfluidic devices," Lab Chip, 2010, 10, 477-483.*

Delaney et al., "Electrogenerated Chemiluminescence Detection in Paper-Based Microfluidic Sensors," Anal. Chem. 2011, 83, 1300-1306.*

John Kennedy, "Nanotech firm makes paper and ink quality displays," SiliconRepublic, Feb. 15, 2005.*

Carvalhal et al., "Electrochemical Detection in a Paper-Based Separation Device," Analytical Chemistry, vol. 82, No. 3, pp. 1162-1165 (Jan. 7, 2010).

Ellerbee et al., "Quantifying Colorimetric Assays in Paper-Based Microfluidic Devices by Measuring the Transmission of Light through Paper," Analytical Chemistry, vol. 81, No. 20, pp. 8447-8452 (Oct. 15, 2009).

Kim et al., "Electrowetting on Paper for Electronic Paper Display," ACS Applied Materials & Interfaces, vol. 2, No. 11, pp. 3318-3323 (Nov. 24, 2010).

Siegel et al., "Foldable Printed Circuit Boards on Paper Substrates," Advanced Functional Materials, vol. 20, No. 1, pp. 28-35 (Jan. 8, 2010).

Supplementary European Search Report for European Application No. 12758368.0, 15 pages (Sep. 7, 2015).

U.S. Appl. No. 12/921,808, filed Mar. 12, 2009, B. Litt, Flexible and Scalable Sensor Arrays for Recording and Modulating Physiologic Activity.

U.S. Appl. No. 12/968,637, filed Dec. 15, 2010, J. Rodgers, High-Speed, High-Resolution Electrophysiology In-Vivo Using Conformal Electronics.

U.S. Appl. No. 13/492,636, filed Jun. 8, 2012, J. Rodgers, Flexible and Stretchable Electronic Systems for Epidermal Electronics.

U.S. Appl. No. 14/155,010, filed Jan. 14, 2014, R. Nuzzo, Methods and Devices for Fabricating and Assembling Printable Semiconductor Elements.

U.S. Appl. No. 14/173,525, filed Feb. 5, 2014, J. Rodgers, Arrays of Ultrathin Silicon Solar Microcells.

U.S. Appl. No. 14/220,910, filed Mar. 20, 2014, J. Rodgers, Controlled Buckling Structures in Semiconductor Interconnnects and Nanomembranes for Stretchable Electronics.

U.S. Appl. No. 14/220,923, filed Mar. 20, 2014, J. Rogers, Stretchable Form of Single Crystal Silicon for High Performance Electronics on Rubber Substrates.

U.S. Appl. No. 14/479,100, filed Sep. 5, 2014, J. Rodgers, Printed Assemblies of Ultrathin, Microscale Inorganic Light Emitting Diodes for Deformable and Semitransparent Displays.

U.S. Appl. No. 14/521,319, filed Oct. 22, 2014, J. Rodgers, Stretchable and Foldable Electronic Devices.

U.S. Appl. No. 12/575,008, filed Oct. 7, 2009, R. Ghaffari et al., Catheter Balloon Having Stretchable Circuitry and Sensor Array.

U.S. Appl. No. 12/972,073, filed Dec. 17, 2010, G. Callsen et al., Methods and Apparatus for Conformal Sensing of Force and/or Acceleration at a Person's Head.

U.S. Appl. No. 12/976,607, filed Dec. 22, 2010, G. Callsen et al., Methods and Apparatus for Conformal Sensing of Change in Motion at an Arbitrarily-Shaped Surface.

U.S. Appl. No. 12/976,814, filed Dec. 22, 2010, G. Callsen et al., Methods and Apparatus Having Power Control Features for Conformal Sensing of Change in Motion of a Body Part.

U.S. Appl. No. 12/976,833, filed Dec. 22, 2010, G. Callsen et al., Methods and Apparatus for Assessing Head Trauma Based on Conformal Sensing of Force and/or Change in Motion of a Person's Head.

U.S. Appl. No. 13/082,388, filed Apr. 7, 2011, B. De Graff et al., Methods and Apparatus for Measuring Technical Parameters of Equipment, Tools and Components Via Conformal Electronics.

U.S. Appl. No. 14/004,408, filed Mar. 9, 2012, R. Ghaffari et al., Integrated Devices to Facilitate Quantitative Assays and Diagnostics.

U.S. Appl. No. 13/481,843, filed May 27, 2012, Elolampi et al., Electronic, Optical and/or Mechanical Apparatus and Systems and Methods for Fabricating Same.

U.S. Appl. No. 13/499,626, filed Jun. 12, 2012, R. Ghaffari et al., Protective Cases With Integrated Electronics.

U.S. Appl. No. 13/550,254, filed Jul. 16, 2012, J. Carbeck et al., Detection of a Force on a Foot or Footwear.

U.S. Appl. No. 13/568,022, filed Aug. 6, 2012, R. D'angelo et al., Catheter Balloon Methods and Apparatus Employing Sensing Elements.

U.S. Appl. No. 13/603,290, filed Sep. 4, 2012, Rafferty et al., Electronics for Detection of a Condition of Tissue.

U.S. Appl. No. 13/631,739, filed Sep. 28, 2012, C. Rafferty et al., Electronics for Detection of a Property of a Surface.

U.S. Appl. No. 13/646,613, filed Oct. 5, 2012, R. Ghaffari et al., Cardiac Catheter Employing Conformal Electronics for Mapping.

(56) References Cited

OTHER PUBLICATIONS

U.S. Appl. No. 13/747,826, filed Jan. 23, 2013, B. De Graff et al., Methods and Applications of Non-Planar Imaging Arrays.
U.S. Appl. No. 13/640,280, filed Feb. 25, 2013, B. De Graff et al., Methods and Apparatus for Measuring Technical Parameters of Equipment, Tools and Components Via Conformal Electronics.
U.S. Appl. No. 13/843,873, filed Mar. 15, 2013, Y. Hsu, Strain Isolation Structures for Stretchable Electronics.
U.S. Appl. No. 13/843,880, filed Mar. 15, 2013, Y. Hsu, Strain Relief Structures for Stretchable Interconnects.
U.S. Appl. No. 13/844,399, filed Mar. 15, 2013, S. Fastert et al., Conformal Electronics Integrated With Apparel.
U.S. Appl. No. 13/844,508, filed Mar. 15, 2013, S. Fastert et al., Monitoring Hit Count for Impact Events.
U.S. Appl. No. 13/844,635, filed Mar. 15, 2013, R. Ghaffari et al., Catheter Balloon Having Stretchable Integrated Circuitry and Sensor Array.
U.S. Appl. No. 13/844,638, filed Mar. 15, 2013, C. Rafferty et al., Embedding Thin Chips in Polymer.
U.S. Appl. No. 13/844,677, filed Mar. 15, 2013, S. Lee et al., Catheter Device Including Flow Sensing.
U.S. Appl. No. 13/844,767, filed Mar. 15, 2013, R. Ghaffari et al., Catheter Balloon Employing Force Sensing Elements.
U.S. Appl. No. 13/963,778, filed Aug. 9, 2013, B. De Graff et al., Systems, Methods and Devices Having Stretchable Integrated Circuitry for Sensing and Delivering Therapy.
U.S. Appl. No. 14/093,329, filed Nov. 29, 2013, R. Ghaffari, Systems, Methods, and Devices Having Stretchable Integrated Circuitry for Sensing and Delivering Therapy.
U.S. Appl. No. 14/147,347, filed Jan. 3, 2014, R. Ghaffari et al., Catheter or Guidewire Device Including Flow Sensing and Use Thereof.
U.S. Appl. No. 14/276,413, filed May 13, 2014, Y. Hsu et al., Conformal Electronics Including Nested Serpentine Interconnects.
U.S. Appl. No. 14/294,808, filed Jun. 3, 2014, Kacyvenski et al., Motion Sensor and Analysis.
U.S. Appl. No. 14/311,686, filed Jun. 23, 2014, Fenuccio et al., Band With Conformable Electronics.
U.S. Appl. No. 14/451,981, filed Aug. 5, 2014, X. Li et al., Flexible Temperature Sensor Including Conformable Electronics.
U.S. Appl. No. 14/488,544, filed Sep. 17, 2014, W. Arora et al., Extremely Stretchable Electronics.
U.S. Appl. No. 14/510,868, filed Oct. 9, 2014, B. Ives, Utility Gear Including Conformal Sensors.
U.S. Appl. No. 25/506,439, filed Oct. 15, 2014, X. Li et al., Electronic Device Having Antenna.
U.S. Appl. No. 14/518,856, filed Oct. 20, 2014, R. Ghaffari et al., Systems, Methods, and Devices Using Stretchable or Flexible Electronics for Medical Applications.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.
U.S. Appl. No. 14/630,335, filed Feb. 24, 2015, B. Keen, Conformal Electronics with Deformation Indicators.
U.S. Appl. No. 14/656,046, filed Mar. 12, 2015, R. Ghaffari et al., Quantification of a Change in Assay.
Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
International Search Report, PCT/US2012/028590, date of mailing Jun. 13, 2012, 2 pages.
Written Opinion, PCT/US2012/028590, date of mailing Jun. 13, 2012, 10 pages.

* cited by examiner

INTEGRATED DEVICES TO FACILITATE QUANTITATIVE ASSAYS AND DIAGNOSTICS

CROSS-REFERENCE TO RELATED APPLICATIONS

This application is the U.S. national stage of International Application No. PCT/US2012/028590, filed on Mar. 9, 2012, which claims priority to and benefit of U.S. Provisional Application No. 61/451,943, filed on Mar. 11, 2011, each of which is incorporated herein by reference in its entirety, including drawings.

BACKGROUND

In the field of health care, and particularly human diagnostics, point-of-care (POC) testing generally refers to laboratory tests outside of a central laboratory. POC has improved patient care efficiency as it allows diagnostic testing to be performed wherever a patient may be, including in some instance by the patent themselves. POC not only provides the patients with convenience of self health monitoring, but also allows remote medical record keeping and diagnoses, for example, by uploading the POC test results to a health professional's site through the Internet.

Impedance-based glucose sensors/test trips together with their dedicated reader apparatuses, such as ONETOUCH® produced by LifeScan Inc., are useful for quantitative assessment of blood glucose levels. The reader apparatuses can provide clear and understandable readouts to users, but usually are expensive and are designed for specific tests.

The cellular device industry's adoption of miniaturized cameras has demonstrated an alternative platform for off-site detection and diagnosis of disease, using colorimetric analysis. Recent studies show that camera phones can be used as portals for acquisition and transmission of images for rapid clinical assessment and treatment recommendations by off-site trained physicians.

Test strips that can be used with a general-purpose mobile terminal, such as a cellular phones (referred to as "glucophones"), eliminate the need for dedicated reader devices. Instead, the cellular phones can be used as general-purpose reader apparatuses for a variety of data readout, analysis, display, and transmission. For example, Healthpia USA has developed a glucose meter ("glucopack"), which replaces the battery cover of a cellular phone. Test strips are inserted into the glucopack to analyze glucose level results.

An existing diagnostic system uses test strips that exhibit color changes when brought in contact with a test sample, such as blood. The color changes of the test strips are read by a dedicated apparatus, or a general-purpose reader apparatus such as a mobile phone. The mobile phone may have the functionality of obtaining the color information of the test strips. The process may involve taking an image of the test strips using a camera of the mobile phone, and then transmitting the image to an external analysis system for data analysis and display to users. The test strips can be illuminated by the ambient light, or with an external light source.

FIG. 1 depicts a schematic diagram of another example of an existing diagnostic system that uses test strips 10 with an application-specific dedicated reader apparatus 20. When a test strip 10 is inserted into the reader apparatus 20, a light source 22 of the reader apparatus sends a light beam 24 to illuminate the detection region of the assay 26 of test strip 10. The assay 26 can include the test sample, a mixture of the sample and a reagent, or a reaction derivative from the sample. The reaction between the sample and the reagent, or a chemical reaction within the sample itself, can be stimulated using an electronic circuit 28. The transmitted light carries the information of the assay 26, such as color or opacity information, and is received by a photodetector 30 and analyzed by the reader apparatus 20.

Although glucophones can aid in diabetes management, they exhibit certain limitations, including added cost of the glucopack compartments, limited compatibility of the glucopack compartments with cellular phone models, and a lack of wireless and signal processing functionality on the paper strips.

Quantitative information relating to a sample also can be used for diagnoses of, for example, HIV, Malaria, etc. When a sample such as blood is placed onto a test strip, a pre-deposited assay changes color and informs the user whether a patient tests positive for an affliction (such as HIV or Malaria).

These existing devices may be prohibitively expensive for certain applications. For example, the reader apparatus might not be widely affordable in developing countries where mobile diagnostics are needed the most. In addition, in an environment such as a battle field, the users might not be able to afford the time to insert the test strip into the reader apparatus, or to carry the reader apparatus around.

SUMMARY

POC testing devices are becoming popular, particularly with the introduction of mobile-phone-based reader apparatuses. Existing devices can present certain disadvantages, including high cost and the requirement of a separate reader with built-in electronics that runs on batteries. In addition, when user visualization of color changes is used as an indication of the reaction in many devices, inaccurate readings can result. For example, where the color change occurs along a gradient, it may not be clear to what degree the assay has changed color. Also, if a diagnostic device is read through on a user's visualization of a color change of a test strip, the assessment may be highly subjective leading to some uncertainty in the diagnostic results.

In addition, current image capture methodologies may not achieve high-accuracy diagnostic capabilities due to a number of practical limitations. For example, the light intensity may not be uniformly encoded across different camera models. Changes in ambient light conditions may necessitate extensive calibration measures. Also, the simple lens configurations could preclude high resolution imaging of near field objects. These may become limiting factors to practical use in areas such as viral load detection where high sensitivity is needed.

As the availability of life-extending treatments for HIV increases, the benefit of accurate monitoring of viral load in patients has become apparent. Traditional qualitative lateral flow tests, such rapid HIV antibody tests, can perform poorly at quantification. Quantification may require a dedicated external reader apparatus that can be bulky and/or expensive.

Achieving the concurrent goals of providing quantitative information of analyte in a digital form, fast and accurate measurements, and reduced cost for diagnostic applications may be challenging based on existing available electronic and optoelectronic systems and devices. Existing semiconductor-based electronic circuits, for example, those integrated with optical components, have relatively high accuracy and employ relatively mature technologies. However, these devices can be expensive, and may not be easily integrated with test strips. A system capable of POC diagnosis with high accuracy and at a low cost would be beneficial.

In addition, existing POC testing may require more than one step. For example, after the user disposes a sample, such as a drop of blood, to a test strip, the user may then need to insert the test strip into the reader apparatus, which analyzes the sample or a derivative of the sample, and displays the test results to the user. A system capable of more straightforward POC diagnosis would be beneficial.

Accordingly, various examples herein describe devices for providing quantitative information relating to a sample.

The devices herein incorporate sensory electronics on a flexible substrate that for providing the quantitative information relating to the sample. The devices may be disposable. Furthermore, the devices need not rely on an external reader apparatus, such as but not limited to a phone or other hand-held mobile device, for performing the sample analysis or quantification, or for providing the quantitative information relating to the sample. In order to use an external reader apparatus for sample analysis, certain regulatory requirements may need to be met beforehand for the reader to be classified as a medical diagnostics device. Given that the devices herein incorporate sensory electronics for providing the quantitative information relating to the sample, an external reader apparatus need not be used for this purpose. In some examples herein, the external reader apparatus may be used to display the quantitative information relating to the sample (which may be used, e.g., to provide a diagnostics outcome).

Example devices herein include a flexible substrate, electronic circuitry and at least one indicator electrically coupled to the electronic circuitry. The flexible substrate includes at least one paper-based portion, at least one elastomeric portion, or at least one plastic portion. The electronic circuitry may be at least partially formed in or disposed on the flexible substrate. The at least one indicator also may be at least partially formed in or disposed on the flexible substrate. The devices also include a sample receiver at least partially formed in or disposed on the flexible substrate. In various examples, the sample receiver may be formed in or disposed on at least one paper-based portion, at least one elastomeric portion, or at least one plastic portion of the substrate, where applicable. The sample may be a biological sample. The electronic circuitry generates an analysis result based on an output signal from the sample or a derivative of the sample. The at least one indicator provides an indication of the quantitative information relating to the sample based at least in part on the analysis result.

In various examples, the at least one indicator may be part of a display. The sample or derivative of the sample may be contacted with a chemical reagent to provide the output signal.

In an example, the device may also include a container to retain the sample formed in or disposed on the flexible substrate. A reagent may be disposed in the container to react with the sample, where an output optical signal that includes at least a color change or electrochemical change is generated representing a degree to which the reagent reacts with the sample, when the sample is present. The electronic circuitry is coupled to the substrate to analyze the output signal and generate at least one analysis result. In this example, the electronic circuitry includes at least one light source to illuminate the reagent and the biological sample, when present, to measure the color change or electrochemical change and provide an output optical signal representing the color change or electrochemical change. The electronic circuitry may also include at least one photodetector to detect the output optical signal and generate an output electrical signal representing the color change or electrochemical change, where the at least one analysis result is based on the output electrical signal. The at least one indicator is coupled to the flexible substrate, and electrically coupled to the electronic circuitry, to provide an indication of the quantitative information relating to the sample based at least in part on the at least one analysis result In various examples where the device includes a container, the device may also includes a channel disposed between the sample receiver and the container to transfer the sample or a derivative of the sample from the sample receiver to the container. The transfer may be through wicking or other capillary action.

In various examples, the quantitative information includes at least one of: a glucose level, a T-cell concentration, a microorganism concentration, a water-based pathogen concentration, a bovine serum albumin (BVA) concentration, a bacterial concentration, a viral load, an antigen level, an antibody level, a diagnosis of tuberculosis, a diagnosis of dengue fever, a cardiac enzyme concentration, and a diagnosis of malaria.

An example of a device according to a principle herein employs flexible or deformable electronics with integrated micro-fluidic channel systems for analyzing analytes, such as biochemical samples of fluids. Integrated with such electronics are one or more indicators, constituting an "onboard human interface," which can accurately and objectively indicate quantitative information of the test results to the user. The microfluidics substrates can be made of a piece of paper or an elastomeric material, and the entire device including the integrated electronics circuitry and the indicator can be made disposable. In an example, the indicator may be part of a display. Such disposable devices can be used as POC diagnostic devices.

The beneficial characteristics of flexible substrates, such as foldable, deformable, or stretchable substrates, including paper-based substrates, elastomeric substrates, or plastic substrates, may be exploited in such a way as to allow the various components of an integrated device that facilitates quantitative assays and POC diagnostics to be formed (e.g., printed on the substrate) in a monolithic process. In an example implementations described further below, reagents for samples to be measured, electronic circuitry for analysis of samples, and one or more indicators to convey analysis results may be monolithically formed on a substrate, thereby significantly mitigating possibly adverse effects due to temperature variations across a device during a measurement of the sample.

Various examples described herein relate to a device that is entirely disposable, including the electronic circuitry and the indicator(s). This is made possible by using a flexible substrate, such as a foldable, deformable, or stretchable substrate, including a substrate that includes paper-based portions, elastomeric portions, or plastic portions. Printing-based technologies may be used to pattern, e.g., the electronic circuitry and/or the container with the reagents. The resulting device can be relatively inexpensive and disposable yet sufficiently accurate and effective devices.

More specifically, in one example implementation relating to providing quantitative information relating to an analyte, a device is provided including a substrate, and electronic circuitry coupled to the substrate to analyze the analyte. The device further includes at least one indicator coupled to the substrate, and electrically coupled to the electronic circuitry, to provide the quantitative information relating to the analyte based at least in part on the analysis.

In one example, a disposable paper-based diagnostic device is embedded with ultrathin, photosensitive electronics for on-chip quantification of via light transmittance detection. This example combines ELISA-based detection for antibodies or antigens as a measure of viral load, using patterned paper diagnostics (e.g., microfluidics inexpensively patterned into paper) and flexible electronics (e.g., photodetectors, amplifiers, LEDs, and antenna). Processes can be employed for creating and manipulating ultrathin (such as <200 μm, for example <100 μm or even thinner) electronics, which has a thickness of 1%-10% of existing devices. These devices are also lower in cost, and more rugged/flexible than alternatives. Printing such sensory electronics along with a battery onto thin paper substrates can create low-cost, disposable devices capable of quantification without the need for an external reader.

In an example, an integrally formed diagnostic device and sensor is provided, which includes a user interface, e.g., in the form of one or more indicators. In one example implementation, multiple reference points or wells are disposed on or formed in the substrate and used as different concentration references. In one non-limiting example, paper is used as the substrate. Paper provides for adhesion of the sample and wicking a fluid in a predetermined direction. The devices can be based on measurements of optical signals (such as a color change), electrochemical signals, electrical signals (such as impedance signals), or acoustic signals (such as a pressure change).

A device according to one example allows for a one-step glucose measurement using a single device that is entirely disposable. The entire device including the onboard data analysis circuitry and indicator can have a low cost, such as about USD $1. Such a cost is comparable to existing test strips which requires an external reader apparatus. Existing reader apparatuses are generally not disposable due to their high cost. Also, measurements made using existing glucose meters may require at least two steps.

The thermal compensation of the circuitry is possible as all components can be printed in the integral process on the single substrate. Thus, measurement accuracy is improved as compared with existing devices using discrete electronic components.

A deformable paper-based microfluidic device can have patterned permeable and impermeable channels. Fluid filters or analyte-binding membranes can be built within the channels. Strategically positioned detection zones can be arranged at given locations in the permeable channels. Arrayed on the surface and/or physically integrated therewith, a plurality of flexible, stretchable and/or foldable electronic devices can be interconnected into a circuitry that remains operative notwithstanding flexing and stretching of the devices.

Stretchable and foldable electronic devices according to a principle herein may be fabricated on a paper substrate and can include, for example, an integrated circuit, a semiconductor, transistor, a diode, a logic gate, arrays of electronic components, an optical system, a temperature sensors, a pressure sensor, electrical-conductivity sensors, electrodes for pH sensors, chemical sensors, sensors for enzymatic activity, resistors, capacitors, passive devices, light emitting diodes (LEDs), photodiodes (PDs), or photodetectors.

An example herein is directed to a device for providing quantitative information relating to a sample. The device includes a substrate, a container at least partially formed in the substrate to retain the sample, electronic circuitry integrated with or coupled to the substrate to analyze an output signal from the sample or a derivative of the sample, and at least one indicator integrated with or coupled to the substrate, and electrically coupled to the electronic circuitry, to provide the quantitative information relating to the sample based at least in part on the analysis.

In another example, a method for obtaining quantitative information relating to a sample is provided. The method includes disposing the sample on a device in a substantially automated, one-step process. The resulting device is disposable.

In another example, a method of making the device is provided. The method including monolithically forming electronic circuitry and at least one indicator over a flexible substrate.

Another example is directed to a device to conduct an assay of an analyte in a biological sample and provide quantitative information relating to the biological sample. The device includes a paper-based substrate, an elastomeric substrate, or a plastic substrate, a container at least partially formed in or disposed on the substrate to retain the biological sample, and a reagent disposed in the container to react with the biological sample. An output signal including at least a color change is generated representing a degree to which the reagent reacts with the biological sample, when the biological sample is present. The device further includes electronic circuitry coupled to the substrate to analyze the output signal and generate at least one analysis result. The electronic circuitry includes at least one light source to illuminate the reagent and the sample, when present, to measure the color change and provide an optical signal representing the color change, and at least one photodetector to detect the optical signal and generate an output electrical signal representing the color change, the output electrical signal constituting the at least one analysis result. The device further includes at least one indicator coupled to the substrate, and electrically coupled to the electronic circuitry, to provide the quantitative information relating to the sample based at least in part on the at least one analysis result.

Another example is directed to a method for conducting an assay of an analyte in a biological sample so as to provide quantitative information relating to the biological sample, the method performed via a device including a paper-based substrate, at least one light source coupled to the paper-based substrate, at least one photodetector coupled to the paper-based substrate, and at least one indicator coupled to the paper-based substrate. The method includes applying the biological sample to the paper-based substrate, the paper-based substrate having a reagent disposed thereon to react with the biological sample, wherein an output signal including at least a color change is generated representing a degree to which the reagent reacts with the biological sample; illuminating the reagent and the sample using the at least one light source to measure the color change and provide an optical signal representing the color change; detecting the optical signal using the at least one photodetector and generating an output electrical signal representing the color change; and providing the quantitative information relating to the sample, via the at least one indicator, based at least in part on the output electrical signal.

It should be appreciated that all combinations of the foregoing concepts and additional concepts described in greater detail below (provided such concepts are not mutually inconsistent) are contemplated as being part of the inventive subject matter described herein. All combinations of claimed subject matter appearing at the end of this disclosure are contemplated as being part of the inventive subject matter described herein. It should also be appreciated that terminology explicitly employed herein that also may appear in any disclosure incorporated by reference should be accorded a meaning most consistent with the particular concepts described herein.

BRIEF DESCRIPTION OF THE DRAWINGS

The skilled artisan will understand that the figures, described herein, are for illustration purposes only, and that the drawings are not intended to limit the scope of the described teachings in any way. In some instances, various aspects or features may be shown exaggerated or enlarged to facilitate an understanding of the inventive concepts described herein (the drawings are not necessarily to scale, emphasis instead being placed upon illustrating the principles of the teachings). In the drawings, like reference characters generally refer to like features, functionally similar and/or structurally similar elements throughout the various figures.

DETAILED DESCRIPTION

Figure 1:
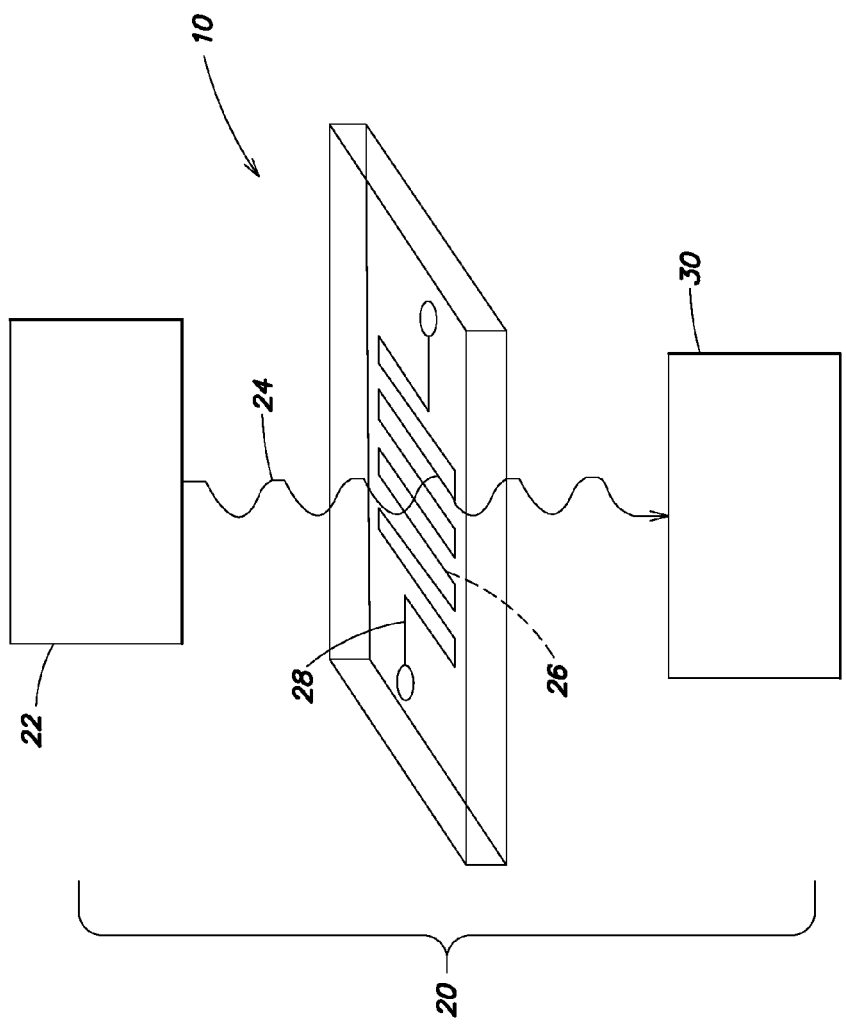
FIG. 1 is a schematic diagram of an example reader apparatus of an example diagnostic system.

Following below are more detailed descriptions of various concepts related to, and examples of, integrated devices and associated methods to facilitate quantitative assays of a sample and diagnostics based on same. It should be appreciated that various concepts introduced above and described in greater detail below may be implemented in any of numerous ways, as the described concepts are not limited to any particular manner of implementation. Examples of specific implementations and applications are provided primarily for illustrative purposes.

As used herein, the term "includes" means includes but not limited to, the term "including" means including but not limited to. The term "based on" means based at least in part on.

Electronic systems embedded in or otherwise integrated with flexible substrates, such as foldable, deformable, or stretchable substrates, including paper-based substrates, elastomeric substrates, or a plastic substrates, have great potential for use in a number of diagnostic applications. Such systems have a thin form factor, flexibility, disposability, and low cost, and thus are suitable for specific applications requiring one or more such advantages.

The use of flexible substrates, such as substrates with elastomeric portions, plastic portions, or paper-based portions, including paper substrates, in some examples of devices and methods described herein is based on recent advancements in paper-based microfluidics systems. Paper-based devices have cost-saving advantages in microfluidics systems. In contrast, existing open-channel microsystems made from glass or polymers can be generally more expensive and less flexible. In a non-limiting example, any of the substrates described herein, including a substrate that incorporates at least one paper-based portion, at least one elastomeric portion, or at least one plastic portion, may be configured to make conformal contact with and adhere to the epidermis (e.g., the epidermis of a human or a non-human animal).

Intricate hydrophilic patterns may be fabricated in paper substrates to exploit the natural affinity of paper to absorb and wick small volumes of fluid via capillary action. Such devices provide the benefits of their small sizes (e.g., smaller than a credit card) and their ability to perform multiple laboratory functions.

Paper-based microfluidics can be different from microfluidics based on other substrates such as a plastic mold or an elastomer, such as (poly)dimethylsiloxane (PDMS). The latter may need external pumping or gravity to transport fluid. By contrast, paper-based devices can be formed to include arrays of channels that allow the fluid to wick through and be transported to one or more reservoirs pretreated with reagents. Chemical reactions can occur at these reservoirs and initiate color changes, whose reflectance and transmittance intensities depend on the concentration of analytes (e.g., glucose and proteins) in the biological fluid samples (e.g., blood, urine, saliva).

Blood glucose concentration tests are identified as a POC diagnostic procedure that can take advantage of the examples described herein. Other diagnostics values that may be measured include, but are not limited to, T-cell (CD4) concentrations in blood, for determining the health of the immune system and the onset of AIDS.

A high accuracy, disposable paper-based microfluidic device according to one example can be used to measure CD4+ T-cell count via impedance spectroscopy. The CD4 diagnostic device contains ultrathin, flexible sensor electrodes, antennae coils, and high performance integrated circuits that enable impedance analysis and short range, wireless power and data transfer with a cellular phone via inductive coupling or RFID. Existing cellular phones/PDAs equipped with RFID functionality can be sufficient for displaying results and serve as a telemetric portal for the data.

CD4+ T-cell count can be estimated by impedance spectroscopy of lysed CD4+ T-cells in hypotonic fluid media. This technology has been demonstrated in microfluidic devices designed with PDMS; however, existing devices may require additional external tubing, syringe pumps or have gravitational flow requirements, and be coupled with amperometric readers to analyze and display the results. Example devices according to the principles herein, described in greater detailed below, can perform functions such as (1) capturing CD4 T-cells in a paper-based microfluidics channel, (2) lysing T-cells, causing a measurable change in impedance induced by the release of intracellular ions, and (3) measuring and wirelessly transferring impedance data to a cellular phone via onboard integrated circuits patterned on paper.

In one example of the disclosure, the microfluidic channels are designed such that test dyes are delivered to the test well site at different times. This can be accomplished simply by varying the distance from dye input zone to test well. This technique can be used to amplify the response due to analyte concentration and is a step in the ubiquitous enzyme-linked immunosorbent assay, such as ELISA tests today.

However, the above are non-limiting examples; a large number of antigens, analytes and enzymes may be measured using sensors and electronics incorporated into paper-based devices according to various examples of the principles herein. The substrate may be formed from other materials and include at least one paper-based portion. Furthermore, although paper is a useful substrate based on its wicking properties, examples disclosed herein are not limited to paper substrates. Other substrate materials such as polymer, elastomer, and glass may also be used.

Many POC diagnostic devices are specified to measure analyte concentrations with only microliter volumes of biological fluid, and should enable accurate diagnosis immediately following the contact with the biological fluid. For example, an existing system exploits movement of fluids across paper strips (i.e., dip stick and lateral flow). Dipsticks use colorimetric tests to detect various biological molecules and function by immersing a paper strip (several centimeters long) into a biological fluid. Lateral flow assays accommodate smaller volumes than dipsticks, and use reagents for specific immunochromatographic assays.

Although lateral flow and dipstick diagnostics can be useful, they can be limited in sensitivity, speed, capability of multiplexing a variety of tests simultaneously, capability of using small volumes of fluid, long-term stability, cost, and ease of disposal. Plastic- and glass-based microfluidic devices present viable alternative methods for more quantitative tests, but they may require fluid pumps and expensive external equipment for external control of flow.

The paper-based microfluidic devices described herein can exploit the full sophistication of inorganic single crystalline semiconductor electronics. In some examples, the fabrication of these devices begins with the formation of ultrathin circuits in planar serpentine geometries. Previously published procedures can be adopted for fabricating the devices described herein.

Alternatively, circuits may be obtained in packaged or unpackaged form and bonded to polymer encapsulated interconnect arrays as previously described in various patent application publications incorporated herein by reference. The electronics can be integrated directly into/onto the substrate, including on the paper-based portion of the substrate, where they are put into contact with detection zones of the microfuidic devices for recording of electrical impedance, absorption of light, acoustic signals, or other signals. Fabrication of microfluidic paper-based devices can be accomplished using photolithographic processes, wax-based printing techniques, or other methods.

The capability of paper-based microfluidic devices and the durability and convenience of integrated deformable electronic components can be realized on a single paper-based "chip." Paper-based micro-fluidic devices can operate without the use of pumps. They can be made of low-cost materials and allow for multiple diagnostic tests to be performed on the same sheet. Incorporating flexible electronics in paper-based microfluidic devices reduces volume of the POC diagnostic systems while maintaining functionality. It also preserves the physical characteristics of paper, which is the accepted medium for POC diagnostics, which may require blood/biological samples.

Accordingly, described herein are non-limiting examples of devices for providing quantitative information relating to a sample. In an example, the device includes a substrate that has at least one paper-based portion, a sample receiver at least partially formed in or disposed on a paper-based portion of the substrate, electronic circuitry and at least one indicator electrically coupled to the electronic circuitry. The electronic circuitry and the at least one indicator are at least partially formed in or disposed on the substrate. The electronic circuitry generates an analysis result based on an output signal from the sample or a derivative of the sample. The at least one indicator provides an indication of the quantitative information relating to the sample based at least in part on the analysis result.

Figure 2:
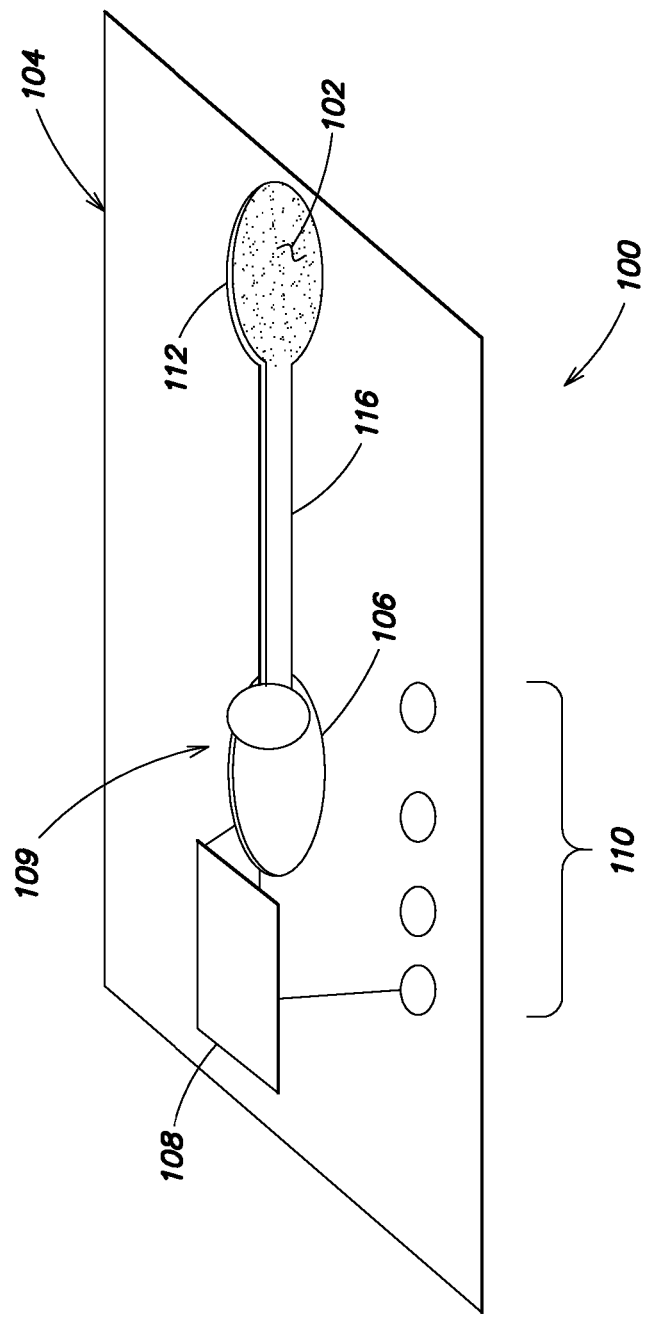
FIG. 2 is a schematic diagram of a device, according to one example, for providing information relating to a sample.

Example structures applicable in any device herein are described. FIG. 2 is a schematic diagram of an example device 100, according to one example, for providing quantitative information relating to a sample 102. The device includes a substrate 104, and a container 106 at least partially formed in or disposed on the substrate 104 to retain the sample 102. The container 106 can be, for example, a well or an indentation formed in the substrate 104. The container 106 can be substantially enclosing a space containing the sample 102, or can have an open top. Electronic circuitry 108 integrated with or coupled to the substrate 104 can be used to analyze an output signal from the sample 102, or from a derivative 109 of the sample 102 to provide an analysis result. The derivative can be an output from a reaction between the sample and a reagent, or results from a reaction within the sample 102 itself (e.g., when the sample 102 is subject to stimulation such as an electrical stimulation or an optical stimulation). The device also includes at least one indicator 110 integrated with or coupled to the substrate 104, and electrically coupled to the electronic circuitry 108, to provide the quantitative information relating to the sample 102 based at least in part on the analysis result. The indicator 110 is readable by a user, and thus serves as a human interface.

The device 100 can further include a receiver 112 formed at least partially in or on the substrate 104 to receive the sample 102. The receiver 112 can be, for example, an indentation or an orifice in the substrate 104. A channel 116 is formed at least partially in or on the substrate 104 to transfer the sample 102 from the receiver 112 to the container 106. A drop of the sample 102, such as a drop of blood, once received by the receiver, can be drawn to the container 106 via the channel 116, by capillary action for example.

In one example, the substrate 104 includes a piece of paper, and the piece of paper is configured to wick the sample from the receiver 112 to the container 106 via a capillary action within the paper. In one aspect, the channel 116 need not necessarily be carved out from the paper; rather, the paper can be engineered, for example, by printing wax on the desired location of the channel, or imprinted or pressed to allow the capillary action to occur in preferred directions.

The substrate 104 can further include PDMS disposed over the paper-based portion. In one example, the PDMS is uncured.

In another example, the substrate 104 further includes a urethane disposed over the piece of paper. The urethane can be UV curable.

The substrate 104 can be very thin, for example, having a thickness on the order of approximately 200 microns or less. This ultrathin structure allows the entire device to be foldable, as described in detail below.

With respect to opposing surfaces of the substrate 104, or other substrates described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom surface of a substrate" does not necessarily require that the indicated surface be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate and each other.

In one example, the device 100 includes a reagent retained in the container 106 to react with the sample 102. The output signal being analyzed indicates a reaction output of the reagent and the sample. The fluidic channel 116 transfers the sample 102 to the container 106 to react with the reagent, forming the derivative 109 being analyzed.

In some examples, the fluidic channel 116 is formed between the piece of paper and a water resistant material. The substrate 104 is formed by bonding the piece of paper and the water resistant material. In one example, the water resistant material includes PDMS.

The substrate 104 may be fabricated upon a variety of materials, such as paper, glass, elastomer, parylene, plastic, polymer, or PDMS.

The device 100 can be used to measure a variety of properties of the sample 102. For example, the quantitative information provided by the indicator 110 can be one of a glucose level, a T-cell concentration, a microorganism concentration, a bovine serum albumin (BVA) concentration, a bacterial concentration, a water-based pathogen concentration, a viral load, antibody level, antigen level, a diagnosis of malaria, tuberculosis or dengue fever, or cardiac enzyme concentration.

The device 100 can be configured as a chemical sensor, where a chemical reaction can be made through electrical or optical stimulation to a sample onboard the device, or to have a reagent to react with the sample. The chemical reaction can cause a change in conductivity, generate an electrical current, or cause a color or opacity change. These changes can be measured as output signals from the sample. In one example, a change in electrical current generated by a sample or its derivative may be measured via a transconductance circuit that converts the current into a voltage.

In some examples, the electronic circuitry 108 further is configured to facilitate generation of the output signal from the sample or the derivative, such as to cause a chemical reaction in the sample or between the sample and a reagent to form the derivative 109.

In some other examples, a reagent or a reaction is not needed. The output signal can be direct optical or electrical measurement of the sample 102. For example, the output signal can be conveyed to the electronic circuitry, or represented, as one of an optical signal, an electrical signal, or an acoustic signal.

In those examples where a reagent is pre-disposed in the container 106 to react with the sample 102, the output signal can represent a degree to which the reagent reacts with the sample. For example, the output signal can be a color or opacity change representing the degree to which the reagent reacts with the sample, an impedance change representing the degree to which the reagent reacts with the sample, or a pressure change representing the degree to which the reagent reacts with the sample. For example, the pressure change can be measured by a piezo-electric pressure sensor. If a modulated stimulus signal is applied to the sample, and the reaction between the sample and the reagent changes a pressure in the sample or derivative, an acoustic wave can be detected using a pressure sensor. If the sample is stimulated with a DC stimulus signal, then a step change in the pressure may be detected.

In one example, the electronic circuitry further includes an analog-to-digital (A/D) converter to convert the reaction output (e.g., the analysis result) to the information in digital form. The A/D converter can be a existing A/D converter functioning in conjunction with a digital-watch type of indicator/display 110. Other methods for communicating the quantitative information can be adopted. These include visible indications such as different types of display modalities, audible, tactile, or vibrational signals.

In some other examples, a comparator and a plurality of references are employed to realize the function of an A/D converter. The output signal represents a value indicative of the quantitative information. The plurality of references are coupled to the substrate, and each have respective different reference values. The comparator compares the value with the plurality of reference values so as to generate the quantitative information.

In one example, the indicator includes a plurality of indicator light emitting diodes (LEDs), coupled to the at least one comparator, to display the quantitative information. For example, the plurality of references correspond to progressively higher reference values. The comparator compares the value progressively with at least some of the plurality of reference values, and each of the plurality of indicator LEDs lights up if the reference value of a corresponding reference is below the value represented by the output signal.

The indicators may include a visual display. The indicators may include other sensory modes or interfaces for displaying quantized values to a user. For example, a vibration or an acoustic signal can indicate that threshold is passed.

In the case that a reagent is pre-disposed in the container 106 to react with the sample 102, the output signal represents a degree to which the reagent reacts with the sample, and the output signal includes a color change representing the degree to which the reagent reacts with the sample. The color change can be, for example, a change in saturation, hue, brightness, or opacity.

In one example, the electronic circuitry includes at least one light source to illuminate the reagent and the sample, when present, to generate the output signal based on the color change, wherein the output signal is an optical signal, and at least one photodetector to detect the optical signal and generate an output electrical signal representing the color change.

The light sources can all solid-state emitting devices including an illumination LED, such as an organic light emitting (OLED). The OLED can be integrally formed with other organic electronic devices on a flexible substrate 104, for example though a direct printing process on a paper substrate.

In one example, the plurality of references each include a reference color, and the electronic circuitry further includes a plurality of reference light sources each to generate a reference optical signal based on the reference color, and a plurality of reference photodetectors each to convert the reference optical signal into a reference electrical signal. The comparator compares the output electrical signal with the plurality of reference electrical signals.

In one example, the plurality of references are integrated with or coupled to the substrate. The comparator compares the output electrical signal with the plurality of reference electrical signals substantially simultaneously.

The device 100 can further include a first filter disposed between the sample and the photodetector to obtain a substantially monochromatic transmission light. In one example, the device 100 further includes a second filter disposed between the light source and the sample. The second filter is not needed if a monochromatic illumination LED is used as the light source.

In some examples, a plurality of second filters are disposed between a broad-band illumination LED and the sample to obtain a multi-channel spectrum of light to illuminate the sample. Spectral information from the sample can thus be obtained. Alternatively, a plurality of narrow-band illumination LEDs can be adopted without the use of the plurality of second filters.

The first and second filters can be made of thin-film polymers having specific dyes disposed thereon. The thin-film polymers can have a thickness of less than 200 microns, such as 50-200 microns.

In one example, the substrate is foldable, and the illumination LED and the photodetector are configured to be substantially aligned with the container by folding the substrate. The device can further include a plurality of alignment marks to aid the folding.

In one example, the output signal includes an impedance of the sample, and the electronic circuitry includes at least one pair of electrodes to measure the impedance of the sample or the derivative. The device can be configured as a glucose meter, for example.

Example devices herein may provide quantitative information relating to a sample or a derivative of the sample based at least in part on analysis of an optical signal from the sample or the derivative.

Figure 3:
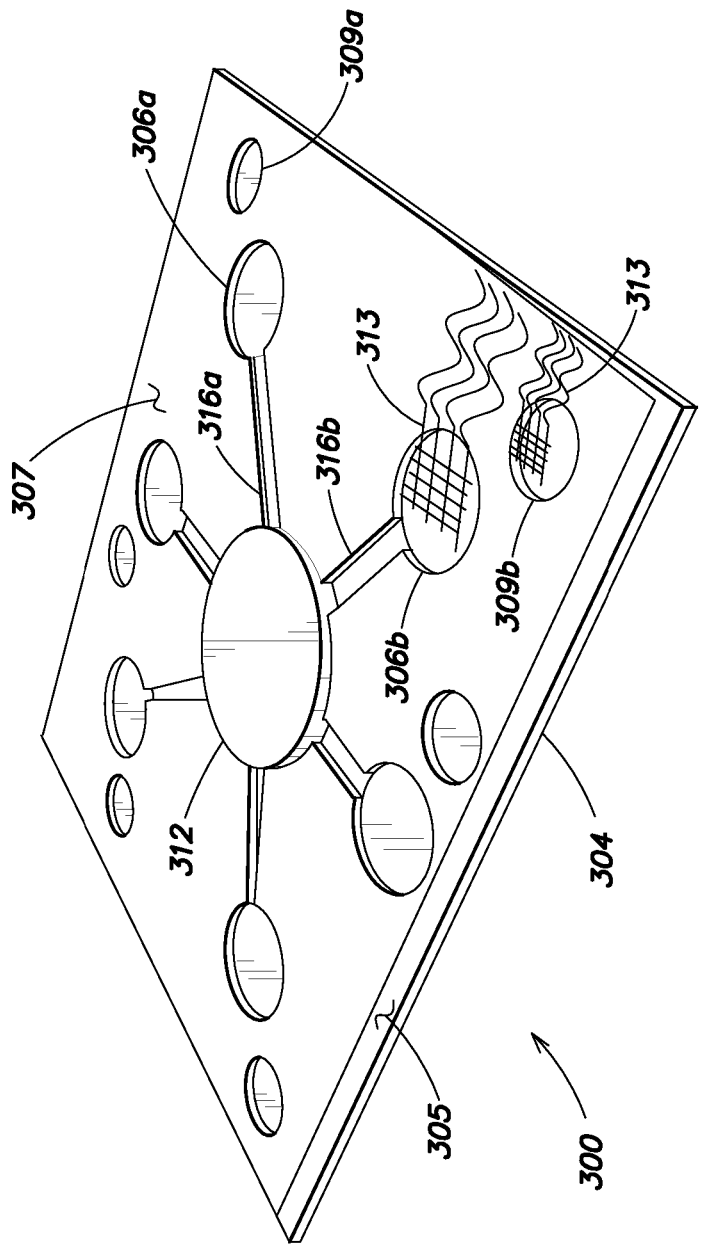
FIG. 3 is a perspective view of a device according to one example.

With reference to FIG. 3, an example device 300 is fabricated over a substrate 304 that includes a piece of chromatography paper 305 and a laminant layer 307. A plurality of containers (e.g., sample wells) 306a, 306b, . . . , are formed in the substrate 304 to retain a plurality of different, or same, samples to be tested. A plurality of reference wells 309a, 309b, . . . respectively correspond to one of the plurality of containers. A single receiver, in the form of an entrance well 312, receives the sample and feeds the sample to the plurality of sample wells 306a, 306b, . . . , through a plurality of corresponding microfluidic channels 316a, 316b, . . . . Each of the sample wells or reference wells has a conformal, micro-scale LED built therein, to illuminate the sample and the reference, respectively, to obtain the quantitative information about the sample. Each well is also equipped with a photodetector such as a photodiode to detect the light transmitted, reflected, or scattered from the sample or the reference.

The device 300 as shown includes an array of 6 pairs of sample/reference wells, but can be scaled to include any number of sample and/or reference wells, such as hundreds to thousands.

In one example, the sample wells have different reagents disposed therein, and are configured to perform different tests for the same sample. For example, one well can be used to test a viral load, and another well can be used to test a bacterial level. The tests can provide binary response, e.g., an indicator LED turns on if a concentration is higher than a specific level. Alternatively, a number of indicators can be included onboard the device to provide quantitative information for each test. Such indicators are described in detail below with respect to FIGS. 13A-19.

In another example, different sample wells test different samples, such a blood sample, a saliva sample, and a urine sample from the same individual, or blood samples from different individuals.

In some examples, PDMS is used as the laminant layer 307. Uncured PDMS can be used to increase the bond strength between devices (e.g., electrodes), and the receiving substrates (e.g., paper). In some other examples, alternatives to PDMS that cure faster and have better adhesion to polyimide encapsulated devices in the absence of an oxide adhesion layer (e.g., Dymax UV curable urethanes) are employed.

The architecture of the device 300 results in improved thermal stability when measuring a sample at the plurality of sample wells and the results are compared with their respective references in the reference wells at close proximity. Thus, relative measurements, rather than absolute ones, are performed. Change in temperature may increase current and may raise the output offset in, e.g., sample well 306*a*, but it would do so locally for the reference well 309*a*, by an equivalent or a proportional amount. This is the same for all sample wells 306*a*, 306*b*, . . . , and their respective references 309*a*, 309*b*, . . . . Potentially adverse affects on measurement due to temperature changes/variations are thus mitigated. The reference dyes are printed and are stable over temperature.

As a result, the measurements are less affected by temperature or internal heating through circuit elements, because any temperature effects are calibrated out by the references at the locations proximate to the respective sample wells. This results in consistent and accurate measurements.

The monolithic fabrication process of the components on the substrate also contributes to the thermal stability. For example, all the components can be printed in a single process on the single paper substrate.

The use of interdigitated layout also reduces the variations in the measurements caused by temperature changes.

The use of a comparator circuit to compare a measurement locally with a reference, instead of using microprocessor, not only reduces complexity and power consumption but also reduces the thermal footprint and thermal instability of the system. For example, several amplifiers can be fabricated monolithically together and generate heat evenly. Thus, changes are shared by all circuits and cancelled out.

In contrast, discrete circuits do not track temperature changes well due to their size and their non-monolithic nature. For example, a discrete circuit has several operational amplifiers in separate packages. They can heat up differently, and errors or temperature-induced variations from one component can ripple through the whole device.

Figure 4:
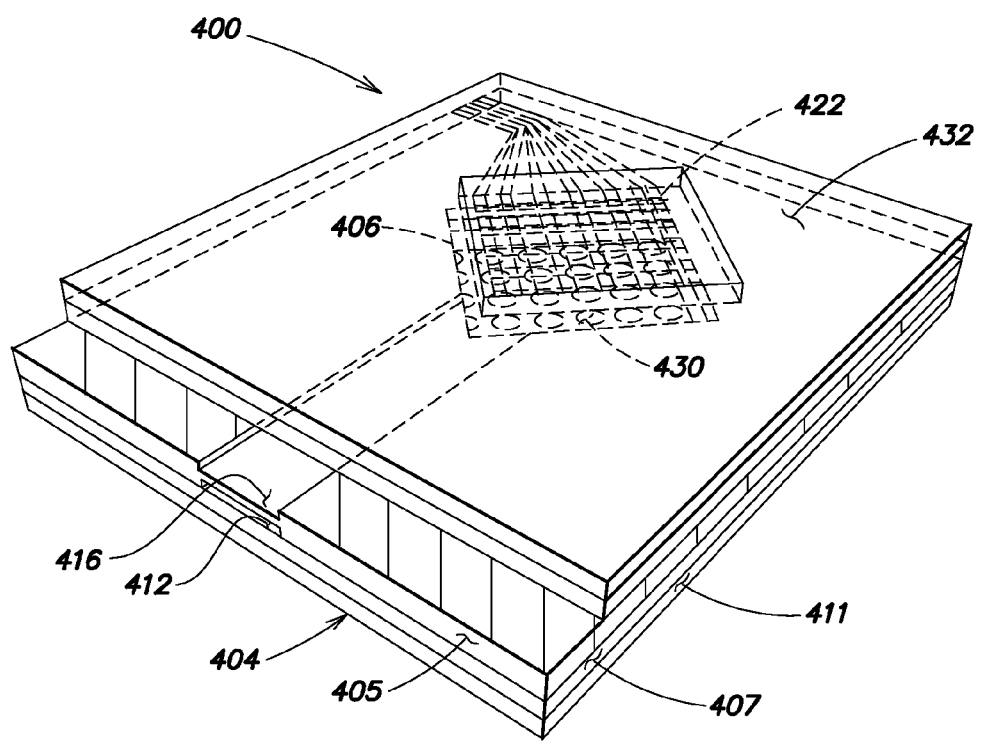
FIG. 4 is a perspective view of a device according to another example.

FIG. 4 is a perspective view of a device 400 according to another example. The device 400 is fabricated over a substrate 404, which includes a piece of chromatography paper 405, a laminant layer 407, and a PDMS layer 411. A receiver 412 is formed on a side of the device 400, in the form of an entrance well. A channel 416 is formed in the piece of paper 405 to transfer a sample disposed at the receiver 412 to a sample well 406. The sample well 406 is sandwiched between a conformal LED 422 and a conformal photodetector 430. The device is covered with a top PDMS layer 432, which encloses the channel 416 and the sample well 406.

In some examples such as in the example illustrated in FIG. 4, the output signal during the measurement can be a change in opacity of the detection region. For example, detection and analysis of light transmission through a translucent paper impregnated with a fluid sample can be performed. The LED 422 can generate a calibrated intensity of light that passes through the detection region of the sample well 406, and the photodetector 430 records the intensity of light received on the other side of the detection region. The amount of light captured depends on the opacity of the sample, or a combination of the sample, the reagent, and the test strip.

Figure 5:
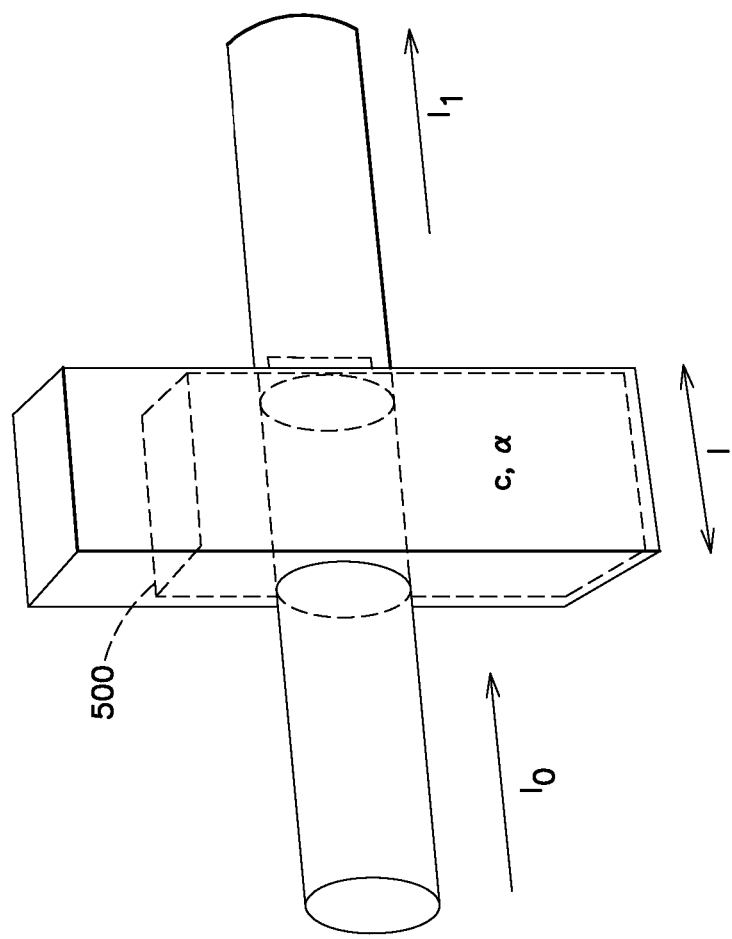
FIG. 5 illustrates the principle of light attenuation through a medium.

FIG. 5 illustrates the light attenuation through a medium 500 (such as the sample well 406 containing the sample therein). The light intensity $I_0$ from the LED 422, after being attenuated by the medium 500 having a thickness of l and an attenuation coefficient α, becomes $I_1$. The transmissivity T of the medium 500 is determined by Beer's law:

$$T = \frac{I}{I_0} = 10^{-\alpha l} = 10^{-\varepsilon l c},$$

wherein ε is a molar absorptivity of the absorber in the medium 500, and c is the concentration of the absorber.

Thus, the opacity in turn is directly related to the concentration of analyte in the assay. As a result of using the onboard LED, the measurements do not depend on ambient light.

This analog signal of the detected light intensity is converted to a digital read out signal by electronics incorporated into the substrate. Alternatively, the detected analog signal may be transmitted (wirelessly or with a wire) to an off-substrate processor for processing.

Figure 6:
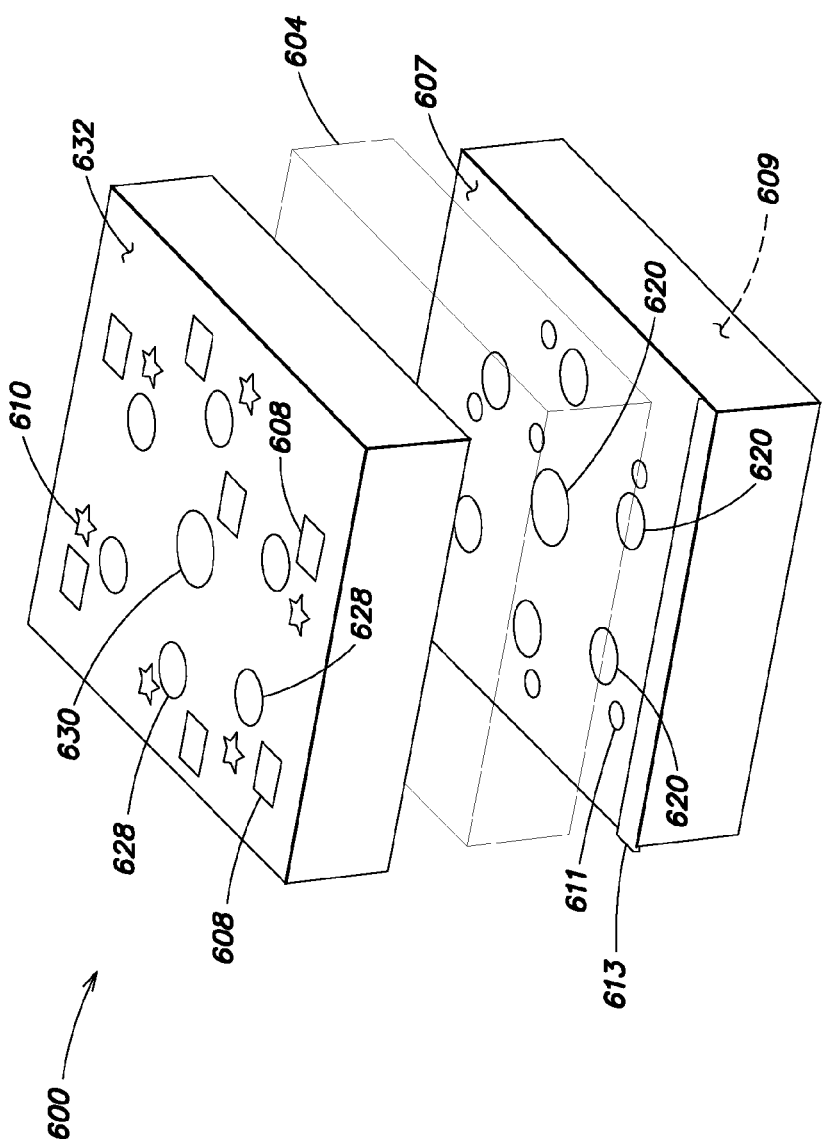
FIG. 6 is an exploded view of a device according to another example.

FIG. 6 is an exploded view of a device 600 according to another example. The device is built upon a substrate 604 in which a sample well and one or more reference wells are formed, as described above in connection with FIGS. 2, 3, and 4 and other figures described below (for ease of illustrating other salient features of the device 600, such wells are not shown in FIG. 6). The substrate 604 can be a piece of paper having fluidics channels formed therein, PDMS, a glass slide, or composed of other materials as described elsewhere herein.

Disposed over the substrate 604 is a top interface layer 632 composed of, for example, an elastomer or a polymer. A photodiode 630 is formed in the top interface layer 632 and overlays the sample well in the diagnostic substrate 604. A plurality of reference photodiodes 628 are also formed in the top interface layer 632 and overlay their corresponding reference wells in the diagnostic substrate 604. It is noted that, in this example, the sample is directly measured in the sample well and compared with the six reference wells, unlike the example illustrated in FIG. 3, where the sample is split and transferred into 6 sample wells and measured therein.

A plurality of photodiode driver and comparator circuits 608 drive the photodiodes 628, 630 and compare the signals detected by the photodiode 630 and the reference photodiodes 628. In one aspect of this example, a plurality of indicator LEDs 610 respectively are disposed adjacent to corresponding reference photodiodes 628 to provide an indication of analysis results (e.g., based on the functionality of comparator circuits 608, described in greater detail below).

A bottom interface layer 607 and the top interface layer 632 sandwich and interface with the substrate 604. The bottom interface layer 607 can be made of polyimide, polyurethane, PDMS, or other elastomeric or polymeric materials. The bottom interface 607 has a plurality of illumination LEDs 620 built therein or disposed thereon, to illuminate the sample and reference wells in the substrate 604. Flexible or stretchable interconnects 609 (not specifically visible in the view of FIG. 6) disposed on or integrated with the bottom interface layer 607 and electrical contacts 611 formed in the bottom interface layer 607 make electrical connections among a thin-film battery 613, the illumination LEDs 620, the circuits 608, the photodiodes 628, 630, and the indicator LEDs 610.

Alternative to the thin-film battery 613, other types of power sources can be included in the device 600. Such a power source may include, for example, a primary battery, a solar cell such as a organic photovoltaic (OPV) cell, an energy-harvesting device such as an inductive coupling coil, etc.

The power source 613 can drive the electronic circuits including the LEDs and the photodetectors with a variety of drive configurations, such as a constant current source, pulse-width modulation (PWM) for control and energy savings, or a buck-boost power configuration.

Figure 7:
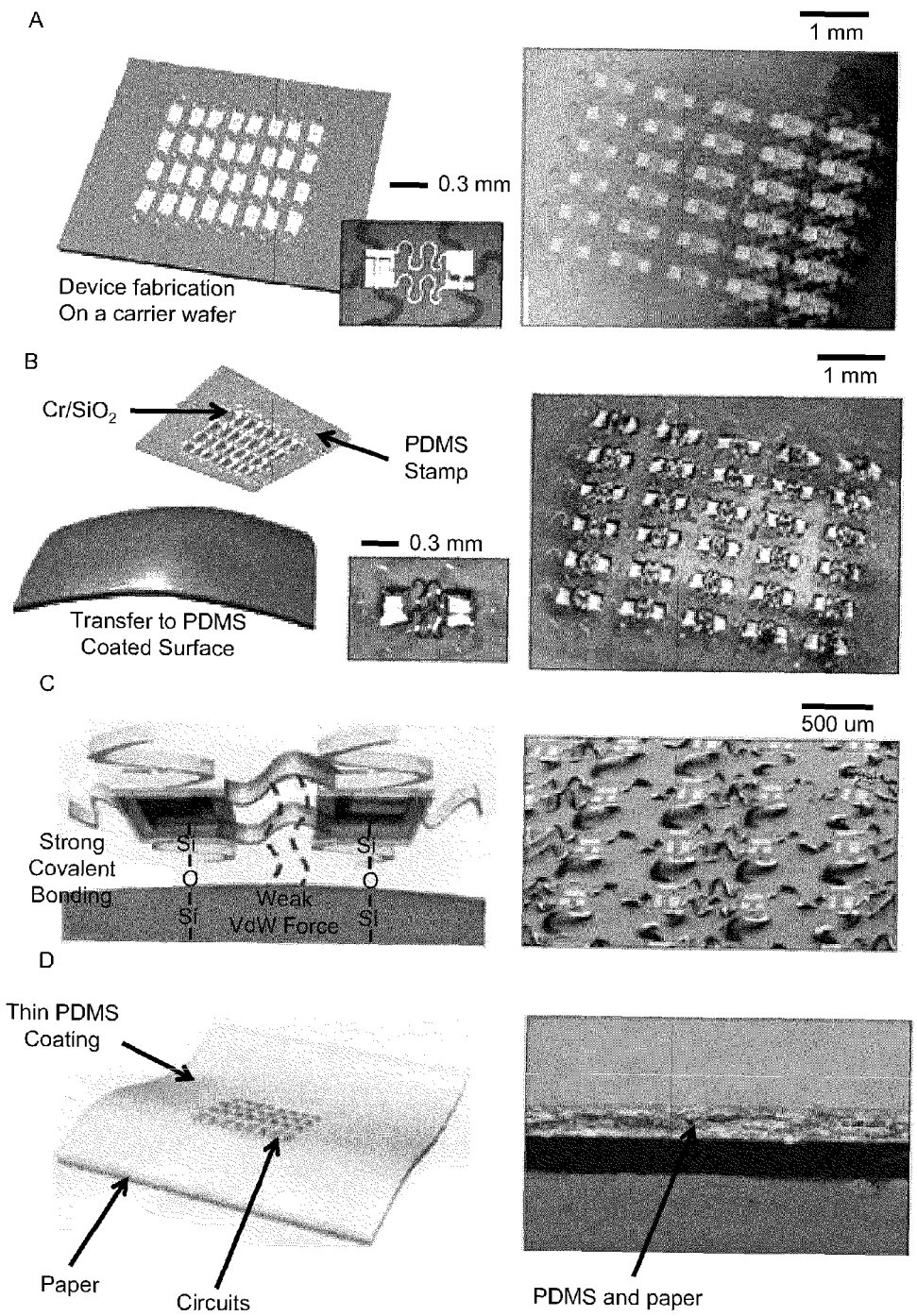
FIG. 7 illustrates a fabrication process of a paper-based diagnostic device according to one example.

Example fabrication methods applicable to any of the devices herein are described. FIG. 7 illustrates a non-limiting example fabrication process of a paper-based diagnostic device, according to one example, in which the electronic circuitry and at least one indicator can be monolithically formed over a flexible substrate.

As illustrated in step A of FIG. 7, the electronic circuitry and at least one indicator are first formed over a carrier wafer. The carrier wafer can be, for example, silicon, silicon-on-insulator (SOI), or glass substrate. The integrated circuits including the metal interconnects, and ultrathin silicon circuitry are removed from the carrier substrate using a PDMS stamp.

In step B, a film of Cr/SiO2 is deposited on the backside of the electronic circuitry and then transferred to a receiving substrate that is coated in PDMS. This Cr/SiO2 film enables the formation of strong covalent bonds as illustrated in panel C of FIG. 7. In panel D, it is illustrated that the integrated circuits transferred to the thin PDMS coating, which is laminated over the paper substrate. Photodiodes and LEDs can also be transferred this way.

In some other examples, the monolithically forming includes forming the electronic circuitry and the at least one indicator over the paper in a single printing process.

Microfluidic devices may be constructed, for example, using techniques developed by Martinez et al: Proc. Natl. Acad. Sci. USA 105, 19606-11 (2008); Lab. Chip. 8, 2146-50 (2008); and Angew. Chem. Int. Ed. Engl. 46, 1318-20 (2007), each of the references being herein incorporated by reference in its entirety.

To form an integrated electronic and microfluidic device, an appropriate patterned-paper platform for the device can be designed and developed. The paper-based substrate can be selected based on wicking speeds, sample retention, consistency and compatibility with the required assay (e.g., glucose oxidase). Biocompatible excipients such as sucrose or trehalose may be used to stabilize enzymes used in the assay. Plasma separation membranes are also selected for the desired diagnostic.

Many other substrates may be used for creating a microfluidic device or device layers. Device layers may be composed of a variety of semi-permeable materials such as porous polymers and elastomers, rigid or flexible nanofiber composites, biologically selective membranes (e.g., fluid mosaic model). Other materials that may facilitate a wicking effect similar to paper can also be used. These materials may include gels with wicking properties, and electromagnetic materials that may be designed to create peristaltic motions to pulse analytes and other fluids to test wells.

Assembly of ultrathin ICs on paper-based microfluidic device may be accomplished with a pick-and-place transfer printing tool, with which electronic circuits are transferred from a carrier wafer to paper substrates or other types of substrates employed for the diagnostic devices. The metal conductive interconnects typically include metal encapsulated in polyimide. In each transfer step, ICs, electrodes, and associated interconnects may be moved from dense arrays on an SOI wafer to sparse arrays on paper. Integration of electrodes and circuits with a paper-based microfluidic platform can be achieved with thin layers (~100 μm) of low modulus PDMS, which encapsulate the electronics and serve as an adhesion layer to the paper microfluidic substrate. Thin film passives (resistors and capacitors) will also be integrated into the circuits by bonding to conductive arrays on the PDMS (ACF bonding, cold welding etc.). Electronic devices (e.g., LEDs, photodetectors, electrodes), in turn, can be preferentially aligned with reaction sites in the micro-fluidic devices to perform analysis.

As another example, Dae-Hyeong Kim et al., Science 333, 838 (2011) describes electronic systems and circuitry that achieve minimal thicknesses, and exhibit effective elastic moduli, bending stiffness, and areal mass densities that can be matched to the epidermis. The electronic system in Kim et al. integrates a collection of multifunctional sensors (such as temperature, strain, and electrophysiological), microscale light-emitting diodes (LEDs), active to passive circuit elements (such as transistors, diodes, and resistors), wireless power coils, and devices for radio frequency (RF) communications (such as high-frequency inductors, capacitors, oscillators, and antennae), on the surface of a thin, gas-permeable elastomeric sheet based on a polyester with a low Young's modulus (see Kim, p. 838). The electronic system and its interconnects exhibit ultrathin layouts, and employ neutral mechanical plane configurations and optimized geometrical designs (see Kim, p. 838). The active elements of the electronic systems use electronic materials such as silicon and gallium arsenide in the form of filamentary serpentine nanoribbons and micro- and nano-membranes (see Kim, p. 838). The electronic systems may be laminated onto the epidermis with conformal contact and adhesion based on van der Waals interactions in a manner that is mechanically invisible to a user.

It is recognized herein that the technology disclosed in Kim et al. may be implemented to fabricate an example electronic circuitry described herein. The electronic systems disclosed in Kim et al. would need to be configured to provide the capabilities described in connection with any of the electronic circuitry described herein. That is, the electronic systems disclosed in Kim et al. would need to be configured to generate at least one analysis result based on an output signal from the sample or a derivative of the sample. For example, to provide the functionality of any of the electronic circuitry described herein, an electronic system of Kim et al. may be configured to include temperature sensors, strain sensors, as well as transistors, light-emitting diodes, photodetectors, radio frequency inductors, capacitors, oscillators, and rectifying diodes. As another non-limiting example, the electronic systems of Kim et al. may be configured to provide solar cells and/or wireless coils to provide options for power supply to any of the example devices described herein.

In addition, although the epidermal electronic systems described in Kim et al. are fabricated to match the elastic moduli and bending stiffness of the epidermis, it is recognized herein that these electronic systems would need to be configured to match the properties of the substrates described herein. For example, the elastic moduli, bending stiffness, and areal mass densities of these electronic systems would need to be configured to match the substrate herein that includes at least one paper-based portion. An example device according to a principle herein may be fabricated by disposing an electronic circuitry described herein, formed using the technology of Kim et al. as described above, on a substrate that includes the one or more paper-based portions. It is recognized herein that the electronic circuitry formed using the technology of Kim et al. would need to be disposed on the substrate such that it is electrically coupled to the at least one indicator. It is recognized herein that the electronic circuitry formed using the technology of Kim et al. also would need to be disposed on the substrate such that it does not interfere with the actions of the sample receiver to receive the sample or with the at least one indicator to provide an indication of the quantitative information relating to the sample. Furthermore, the electronic circuitry would also need to allow for any wicking of the sample or sample derivative from the sample receiver to a container and any reaction of the sample or sample derivative with reagents. In a non-limiting example of a device described herein, the device may be fabricated such that the substrate that includes the at least one paper-based portion makes conformal contact with and adhere to an epidermis, e.g., the epidermis of a human or a non-human animal.

Any other applicable technique may be employed to fabricate a device according to the principles described herein. As non-limiting examples, the following patent publications (which are hereby incorporated herein by reference in their entireties, including drawings) describe applicable techniques that can be used for device fabrication:

U.S. publication no. 2006 0038182-A1, published Feb. 23, 2006, filed Jun. 2, 2005, and entitled "STRETCHABLE SEMICONDUCTOR ELEMENTS AND STRETCHABLE ELECTRICAL CIRCUITS;"

U.S. publication no. 2008 0157234-A1, published Jul. 3, 2008, filed Sep. 6, 2006, and entitled "CONTROLLED BUCKLING STRUCTURES IN SEMICONDUCTOR INTERCONNECTS AND NANOMEMBRANES FOR STRETCHABLE ELECTRONICS;"

U.S. publication no. 2010 0002402-A1, published Jan. 7, 2010, filed Mar. 5, 2009, and entitled "STRETCHABLE AND FOLDABLE ELECTRONIC DEVICES;"

U.S. publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. publication no. 2010 0116526-A1, published May 13, 2010, filed Nov. 12, 2009, and entitled "EXTREMELY STRETCHABLE ELECTRONICS;"

U.S. publication no. 2010 0178722-A1, published Jul. 15, 2010, filed Jan. 12, 2010, and entitled "METHODS AND APPLICATIONS OF NON-PLANAR IMAGING ARRAYS;"

U.S. publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS;"

U.S. publication no. 2010-0298895, published Nov. 25, 2010, filed Dec. 11, 2009, and entitled "SYSTEMS, METHODS AND DEVICES USING STRETCHABLE OR FLEXIBLE ELECTRONICS FOR MEDICAL APPLICATIONS;" and PCT publication no. WO 2010/102310, published Sep. 10, 2010, filed Mar. 12, 2010, and entitled "SYSTEMS, METHODS, AND DEVICES HAVING STRETCHABLE INTEGRATED CIRCUITRY FOR SENSING AND DELIVERING THERAPY."

Figure 8:
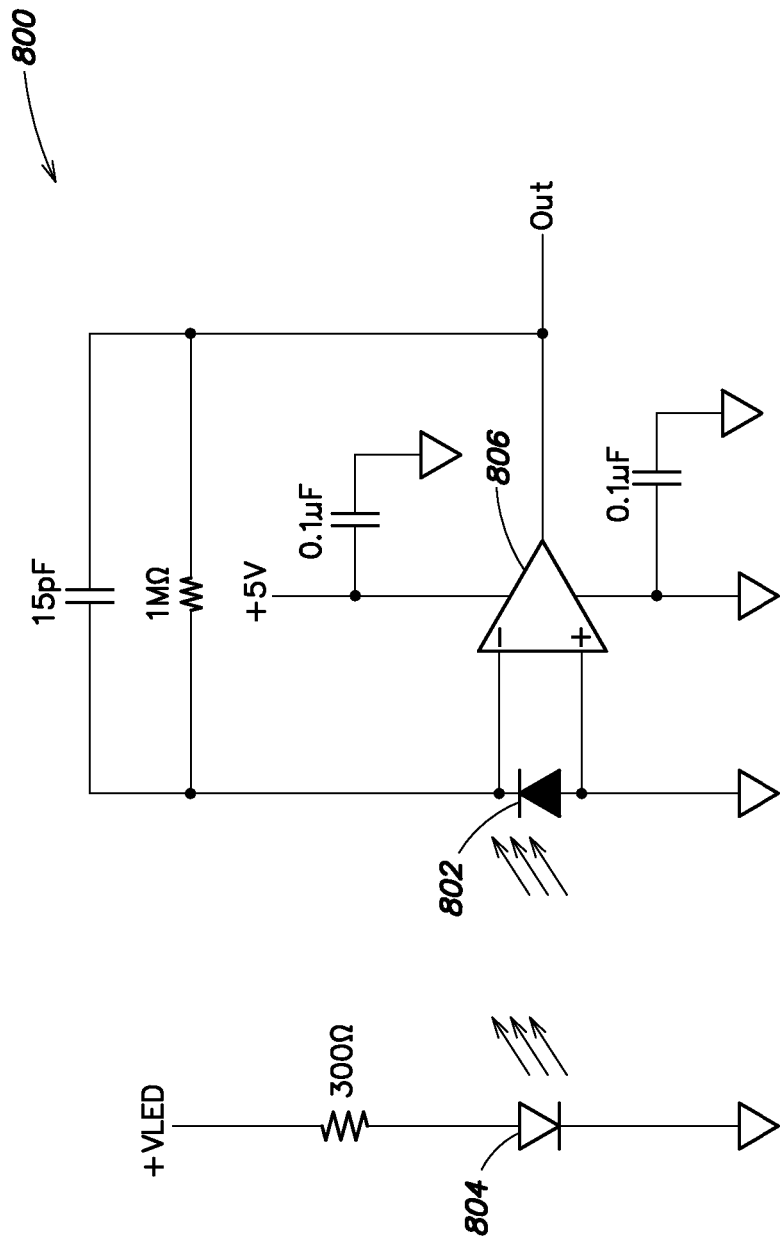
FIG. 8 illustrates an example electronic circuit diagram of a photodiode circuit for use in a device according to one example.

Examples of photodetector circuitry applicable to any of the devices herein are described. FIG. 8 illustrates a non-limiting example of a circuit diagram of the photodetector circuit 800, which can be part of the circuitry 608 illustrated in FIG. 6. In one example, a HAMAMATSU® S6430 photodiode 802 (Hamamatsu Photonics, Shizuoka Japan), which is sensitive to red light, is used to receive red light emitted by a red LED 804 (e.g., representative of one of the LEDs 620 shown in FIG. 6), such as a LUMEX® SSL-LXA 228 SIC LED (Lumex, Inc., Palantine, Ill.). An operational amplifier 806, such as an AD® 8605 op amp (Analog Devices, Norwood, Mass.), is used to amplify the output electrical signal from the photodiode 802.

Generally speaking, the LED, photodiode, and supporting circuitry illustrated in FIG. 8 are configured an optical detection channel, in which the LED and photodiode may form a substantially matched pair of an optical generator and detector. The photodetector can be selected to be substantially sensitive to the color band/wavelength(s) of radiation generated by the light source. For example, a photodiode sensitive to the same color as the illumination LED may be used to detect the as much light from the illumination LED as possible. In the example shown in FIG. 8, a red-sensitive detector and a red illumination LED are adopted, but is should be readily appreciated that substantially matched pairs of LEDs-photodetectors for optical detection of other colors/wavelength regions may be employed in devices according to various examples described herein.

Particular colors/wavelengths of interest for an optical detection channel may be based, at least in part, on one or more of the nature of the sample (e.g., analyte) to be measured/analyzed, the reagent employed, expected concentrations of analyte, and expected degree of reaction based on the particular reagent employed. Accordingly, in some example implementations of the concepts described herein, integrated devices for quantitative assays and diagnostics may include LED-photodecter pairs and supporting circuitry to provide optical detection channels sensitive to particular colors/wavelength bands based on a particular type of sample for which the device is configured to provide quantitative information.

Measurements of an example device according to a principle herein are described in connection with FIGS. 9 and 10.

Figure 9:
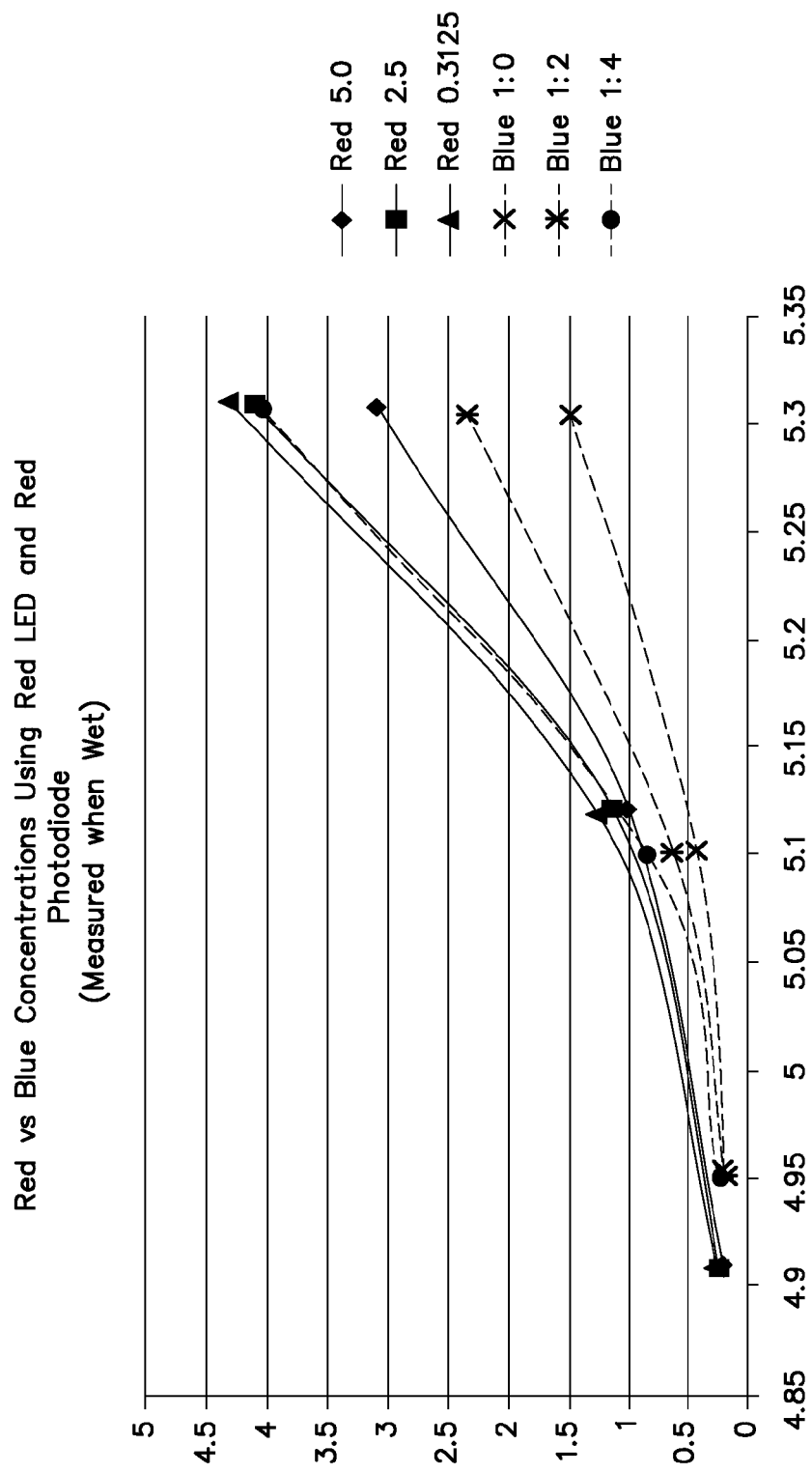
FIG. 9 illustrates experimental data measured using a red LED and a red photodiode, for a red sample and a blue sample, respectively.

FIG. 9 illustrates experimental data measured using a red LED and a red photodiode, for a red sample (i.e., an output signal constituting a red color from a sample or sample/reagent combination) and a blue sample (i.e., an output signal constituting a blue color from a sample or sample/reagent combination), respectively. As shown, for a red sample, measurements using the red LED and the red photodiode produce curves that are not as spread apart as those of the measurements on the blue sample. The color contrast appears to improve the measurement accuracy and resolution.

In a non-limiting example, the derivative 109 from the sample, or from the sample and the reagent, can be configured to have a color that is substantially different from the color of the illumination LED, such that the derivative 109 absorbs as much light as possible from the light source, to improve detection sensitivity. In one example, a blue assay is adopted for use with a red illumination LED. In another example, a blue illumination LED is employed by the device 100 for use with a predominantly red derivative or sample (e.g., blood).

In another example, the measurements can be made within seconds of the sample being applied to or disposed over a device (e.g., in the case of a substrate with paper-based portions, while the paper is still wet) to provide more consistent results. In addition, in some implementations, making measurements from the same side of the paper as the sample is dropped may also improve the measurement accuracy.

Figure 10:
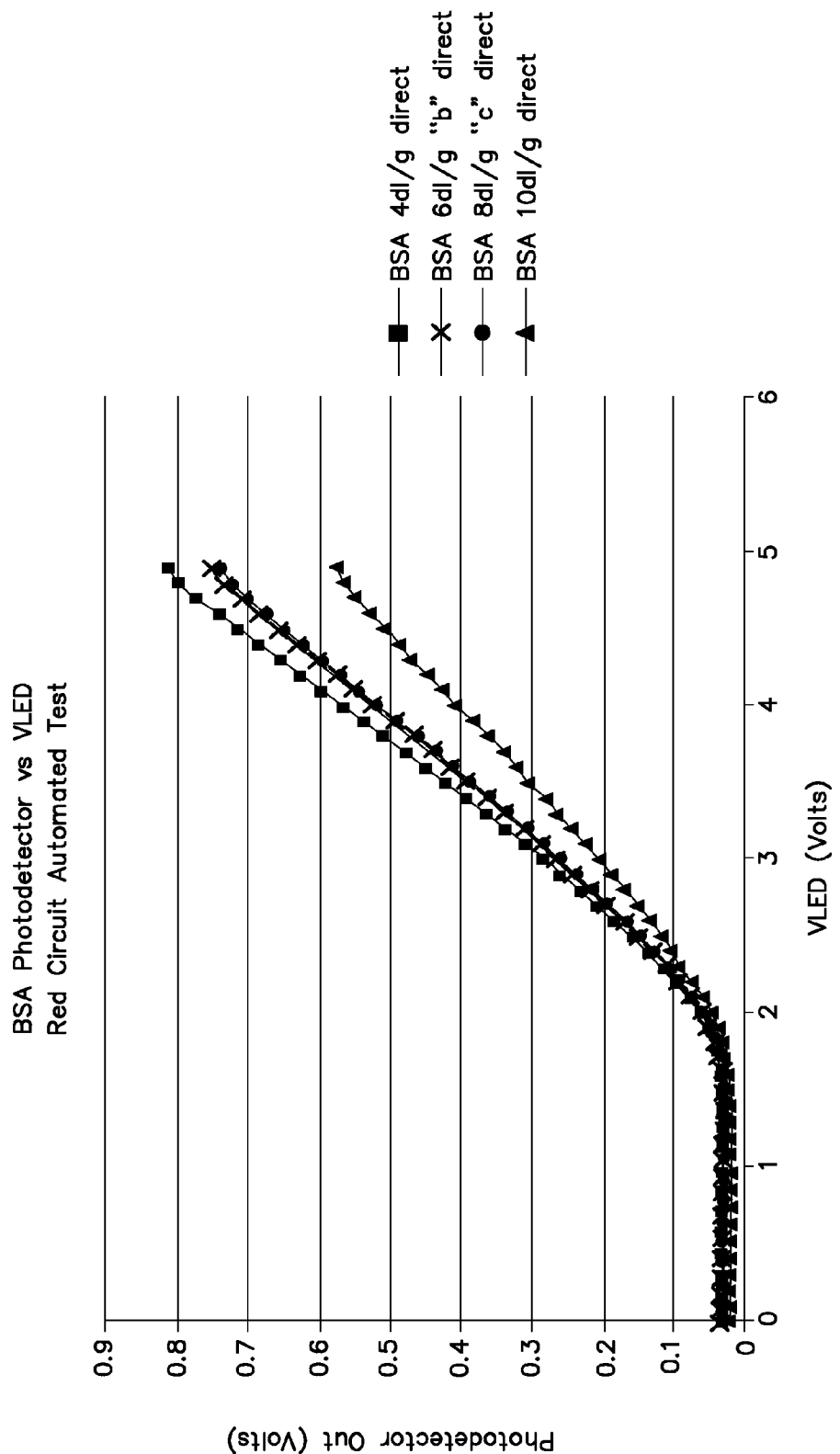
FIG. 10 illustrates photodetector output voltages measured as functions of biases applied to the illumination LED, for various BSA concentrations in the samples.

FIG. 10 illustrates photodetector output voltages measured as functions of biases applied to the illumination LED ($V_{LED}$), for various BSA concentrations in the samples. For a given $V_{LED}$, it can be seen that the output signal is generally stronger for higher BSA concentrations, although such a relationship is not linear at BSA concentrations of 6 dl/g and 8 dl/g.

Example comparators applicable to any of the devices herein are described.

Figure 11A:
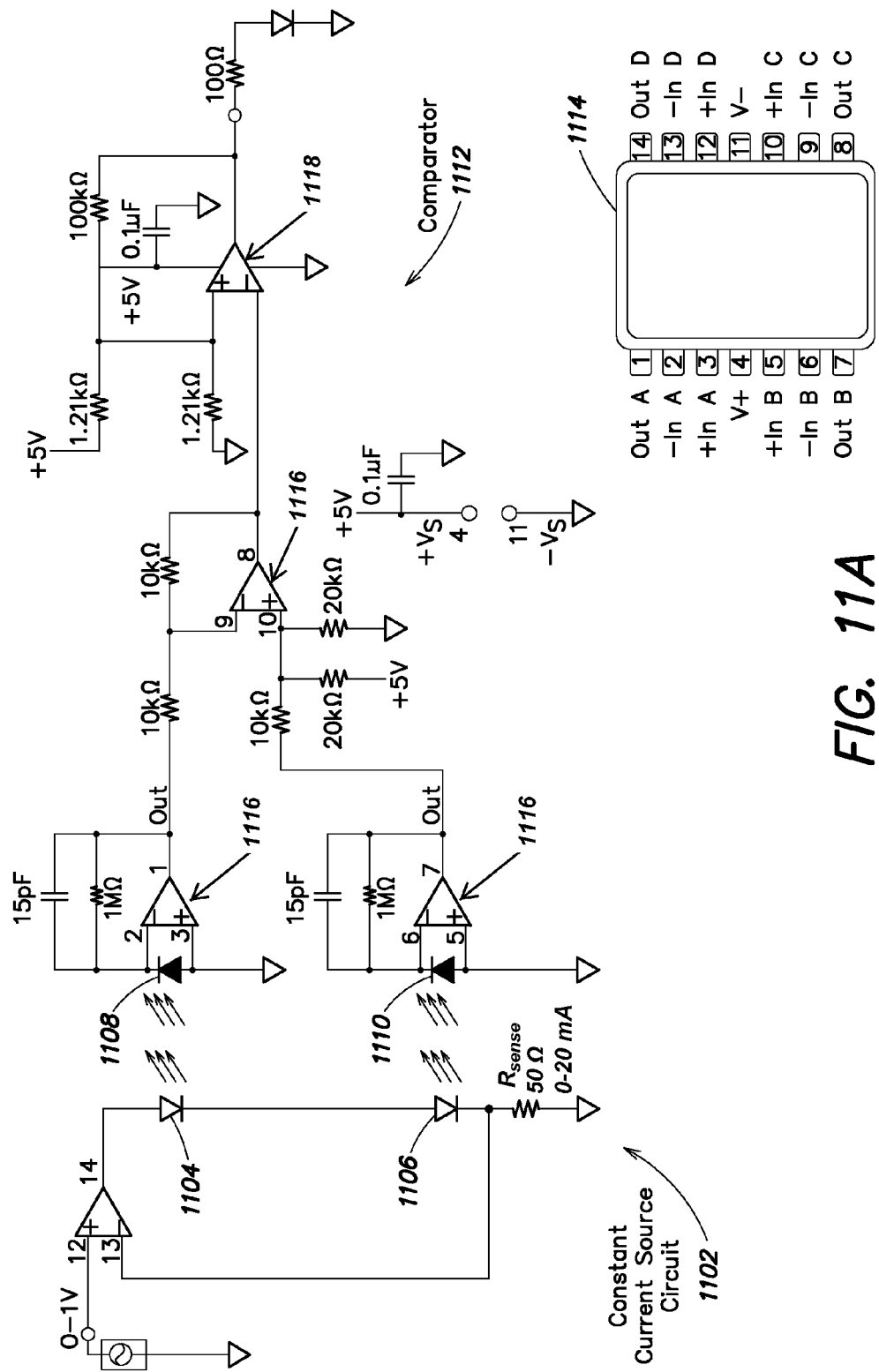
FIGS. 11A and 11B illustrate electronic circuit diagrams of example comparators that may be included in a device according to one example.

FIG. 11A illustrates a circuit diagram representing multiple optical detection channels based on LED-photodetector pairs, as described above, together with a comparator that compares output signals between two such detection channels, according to one example. In example implementations, one of the detection channels illustrated in FIG. 11A would be dedicated to a sample including an analyte that is the subject of the assay, and the other detection channel would be associated with a reference well/sample dye. As shown in FIG. 11A, a constant current source circuit 1102 drives a sample illumination LED 1104 and a reference illumination LED 1106, which illuminate the sample and a reference dye, respectively. A blue LUMEX® SSL-LX A228 USBC-TR11 LEDs (Lumex, Inc., Palantine, Ill.) may be used for illumination LED 1104 or reference illumination LED 1106. The transmitted, reflected, or scattered light from the sample and the reference dyes are received by the sample photodiode 1108 and the reference photodiode 1110, respectively. A blue HAMAMATSU® S6428 photodiode (Hamamatsu Photonics, Shizuoka Japan) may be used for sample photodiode 1108 or the reference photodiode 1110. Operational amplifiers 1116, such as an AD® 8694 op amp (Analog Devices, Norwood, Mass.), may be used. Operational amplifier 1118 may be a MAX® 9031 op amp (Maxim Integrated Products, Sunnyvale, Calif.). The photocurrents from these photodiodes, after being amplified by their respective amplifiers, are compared by comparator 1112. The inset shows various pins 1114 of an example 14-Lead TSSOP (Fairchild Semiconductor, San Jose, Calif.) for the electrical connections with components of the electronic circuit.

Figure 11B:
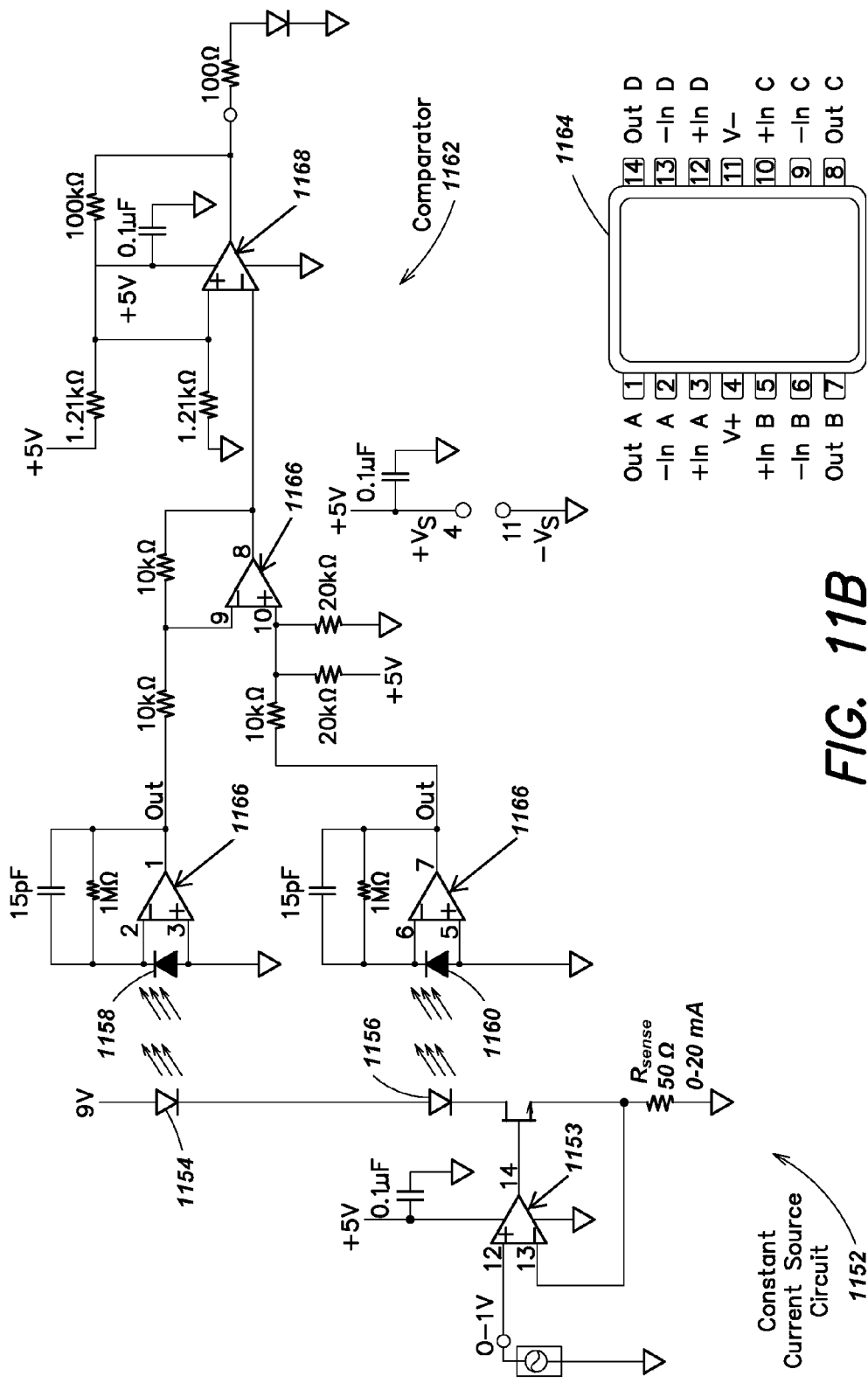

FIG. 11B illustrates a circuit diagram representing multiple optical detection channels based on LED-photodetector pairs, as described above, together with a comparator that compares output signals between two such detection channels, according to another example. Similar to the electronic circuit of FIG. 11A, one of the detection channels illustrated in FIG. 11B may be dedicated to a sample including an analyte that is the subject of the assay, and the other detection channel would be associated with a reference well/sample dye. As shown in FIG. 11B, a constant current source circuit 1152 drives a sample illumination LED 1154 and a reference illumination LED 1156, which illuminate the sample and a reference dye, respectively. A blue LUMEX® SSL-LX A228 USBC-TR11 LEDs (Lumex, Inc., Palantine, Ill.) may be used for illumination LED 1154 or reference illumination LED 1156. The electronic circuitry of FIG. 11B is modified over the electronic circuitry of FIG. 11A to include operational amplifier 1153, to reduce the possibility of saturating LEDs 1154 and 1156. Operational amplifier 1153 may be an AD® 8694 op amp (Analog Devices, Norwood, Mass.). The forward voltage on LEDs 1154 and 1156 can be 3.5V to 4V in operation. The transmitted, reflected, or scattered light from the sample and the reference dyes are received by the sample photodiode 1158 and the reference photodiode 1160, respectively. A blue HAMAMATSU® S6428 photodiode (Hamamatsu Photonics, Shizuoka Japan) may be used for sample photodiode 1158 or the reference photodiode 1160. Operational amplifiers 1166, such as an AD® 8694 op amp (Analog Devices, Norwood, Mass.), may be used. Operational amplifier 1168 may be a MAX® 9031 op amp (Maxim Integrated Products, Sunnyvale, Calif.). The photocurrents from these photodiodes, after being amplified by their respective amplifiers, are compared by comparator 1162. The inset shows various pins 1164 of an example 14-Lead TSSOP (Fairchild Semiconductor, San Jose, Calif.) for the electrical connections with components of the electronic circuit.

Figure 12:
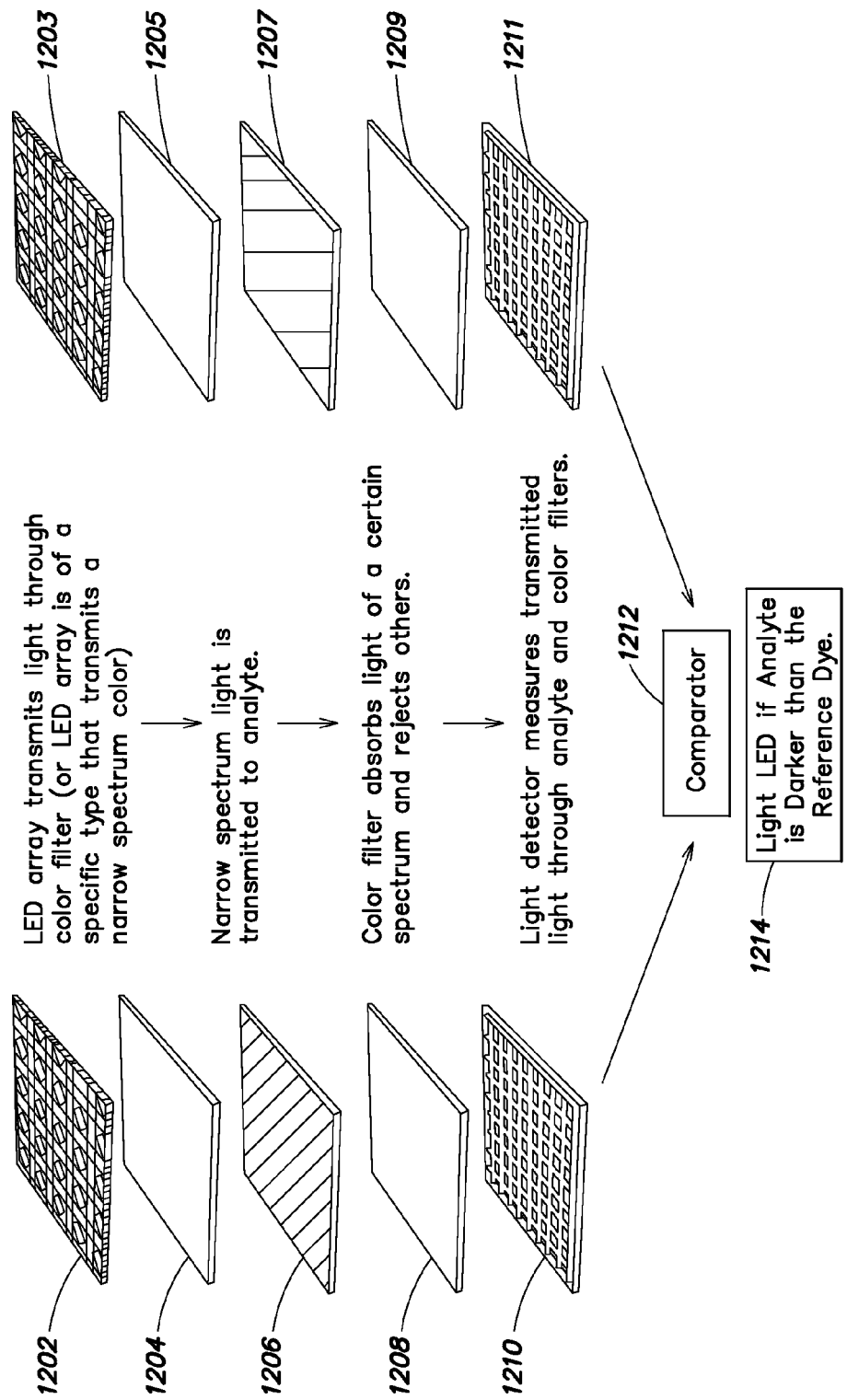
FIG. 12 illustrates light transmission, filtering, detection, and comparison processes performed on a device according to one example.

FIG. 12 illustrates light transmission, filtering, detection, and comparison processes performed on a device according to one example.

To improve performance of the device, e.g., to improve the signal-to-noise ratio (SNR) of detected signals in an optical detection channel, the most relevant spectrum band may be analyzed. Accordingly, in some examples, one or more color filters may be employed in an optical detection channel, together with an illumination LED and corresponding photodetector. The color references and the color of the reagent or assay can be designed taking into account the available filters to provide appropriate SNR in the optical detection channel to ensure effective measurements.

As illustrated in FIG. 12, for a substantially blue sample 1206, preferably red light is used for the measurement. To achieve this, light from an array of broadband illumination LEDs 1202 is filtered with a substantially red filter 1204. Alternatively, narrow-band illumination LEDs emitting substantially in the red spectrum can be used without the need of the filter 1204.

In some other examples, a plurality of filters, or an array of filters, can be used in conjunction of the broadband illumination LEDs to generate light with a spectral distribution to illuminate the sample 1206. Spectral analysis of the sample 1206 can thus be obtained.

Another filter 1208 can be used to reject light of colors different from that of the light illuminating the sample 1206. For example, the filter 1208 can be substantially red, to reject light of colors, so as to improve the SNR at the photodetector 1210. Alternatively, the photodetector 1210 can be selected to be sensitive only to red light, and the second filter 1208 may not be needed.

Each reference well is also equipped with a reference LED 1203, a first reference filter 1205, a reference dye 1207, a second reference filter 1209, and a reference photodetector 1211. The photodetector measures the light intensity by converting the light into an electrical current, which can be amplified by a transconductance amplifier. A quantizer performs an A/D conversion, for example, by making several comparisons simultaneously. That is, the signals output from the photodetector 1210 for the sample and from the reference photodetector 1211 for the reference dye are compared by a comparator 1212, and an indicator LED 1214 lights up if the sample 1206 is darker than the reference dye 1207.

The ultrathin array of photodetectors 1210 and 1211 in planar serpentine geometries can be fabricated using any method in the art, including the method illustrated in FIG. 7, or described in Kim et al., or any of the publications incorporated by reference herein. Metal interconnections between the photodetector array and filters/amplifiers, battery, and LEDs can be achieved during the fabrication process. By building transistors on the same substrate in close proximity, and taking care to place the semiconductor devices such as transistors in specific areas to minimize thermal drift, mechanical stress and drift and using techniques to optimize device matching, high performance A/D conversion can be achieved using this technique.

In general, the reference dyes are calibrated such that their light transmission property is substantially the same as the sample at a certain concentration. For example, three reference dyes can be made to have light transmission properties each mimicking the sample at 10%, 20%, or 30% concentrations. Comparisons can be made against each of the dyes. By using different reference dye values, the concentration of the sample can be derived or interpolated.

Each reference dye will be "interrogated," i.e., compared with the sample to determine whether a reference concentration corresponding to the reference dye is higher or lower than the concentration of the sample, until the concentration of the sample is comparable to that represented by the reference dye. Since the reference dye represents a known concentration, the concentration of the sample can be quickly determined using this comparison method, and the indicator corresponding to the reference dye can light up.

Example indicators applicable to any of the devices herein are described.

Figure 13A:
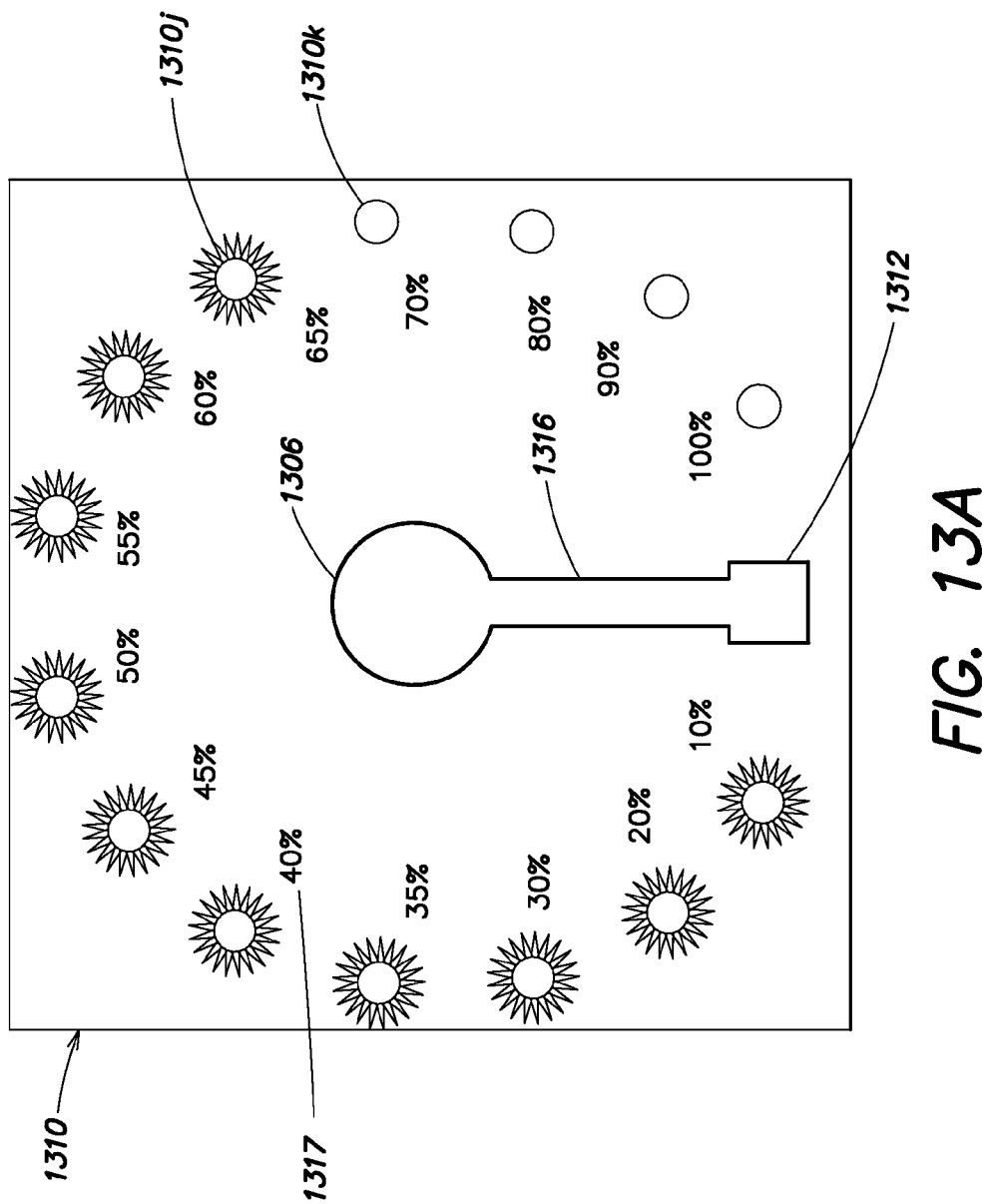
FIGS. 13A and 13B are schematic diagrams of an indicator having a plurality of indicator LEDs arranged in a substantially circular configuration, according to one example.

FIG. 13A is a schematic diagram of an indicator 1310 having a plurality of indicator LEDs 1310*j*, 1310*k*, ... arranged in a substantially circular configuration, e.g., mimicking meter dials. As a sample is received by the device from the entrance well 1312 and wicked into the sample well 1306 through the channel 1316, the concentration of an analyte in the sample is measured, and at least some of the LED indicators light up indicating the measured concentration. For example, if the indicator LED 1310*j* corresponding to a concentration of 65% lights up while its neighboring indicator LED 1310*k*, which corresponds to a concentration of 70% does not, the user can readily visualize that the concentration as measured is between 65% and 70%.

The reference labels 1317 can be printed on the substrate of the device. The scales can be changed by reprinting, while the electronic circuit design can remain the same, thereby significantly reducing cost when a production line switches to manufacture a new batch of devices for different measurements.

Figure 13B:
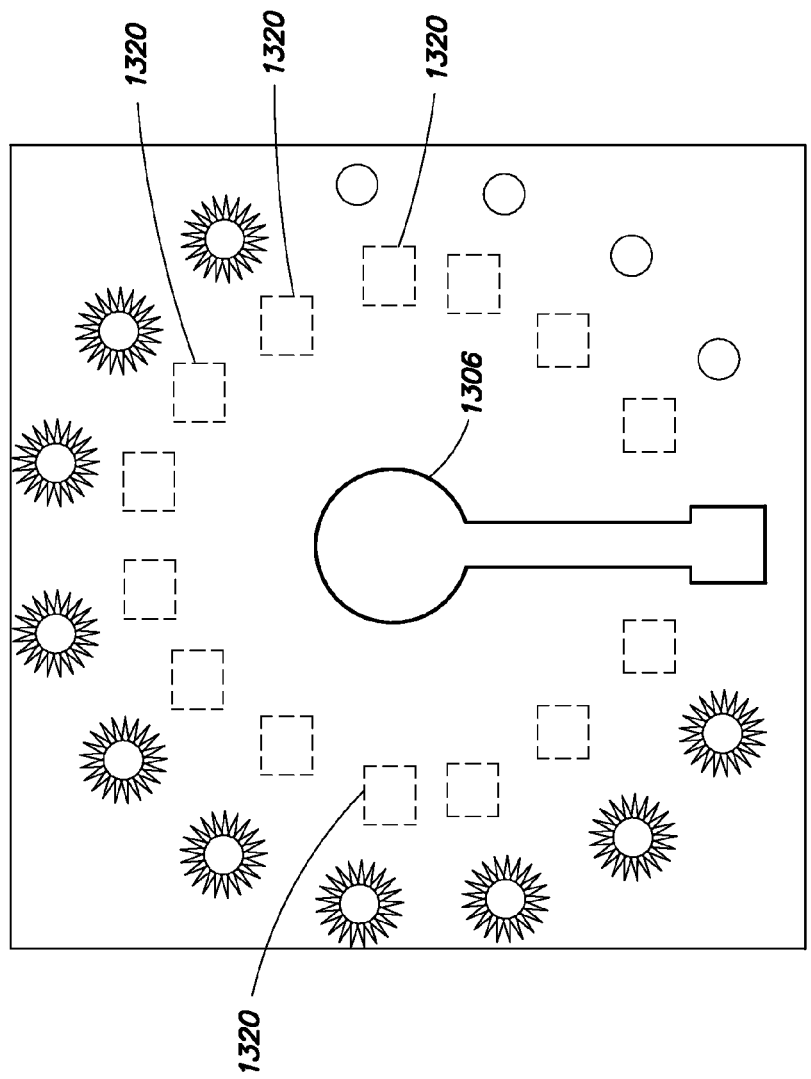

FIG. 13B further illustrates the relationship between the indicator LEDs and the reference dyes. The reference dyes can also be printed on the substrate. Different reference dyes 1320 and/or reference labels 1317 may be printed to allow for analysis of other analytes, or for analysis of other concentrations of analytes. Each indicator LED displays the result of a comparison between the transmitted light through the respective reference dye 1320 and the transmitted light through the analyte in the sample well 1306. The reference dyes 1320 are calibrated for various analyte concentrations, such as at 10%, 20% ... 100% concentrations. Comparisons can be made against each of the dyes, for the opacity and/or color.

In contrast to existing integrated circuit schemes including A/D converters and complex displays for displaying the results in digital form, the simple comparator and indicator design described herein is effective yet having a lower power consumption and lower cost.

In one example, antigen concentration levels in the sample can be detected via ELISA that causes a colorimetric change. Quantification can be determined using color intensity and/or opacity of the sample by measuring the photoelectric signals using the photodetectors. In some examples, illumination of the sample can be provided by ambient light. In some other examples, onboard illumination LEDs provide lighting, and the measurements can be performed in a light or dark environment.

The light intensity versus concentration curves relating concentration to transmittance can be determined in a laboratory setting, and the calibrated reference dyes can then be printed on the devices.

The number of reference dyes is selected based on the desired resolution. In one example, a 10 bit conversion is desired, and 10 reference colors are included onboard the device. Several different diagnostic devices can be made using the same electronics mask design. The analyte or reagent can be changed. For example, instead of testing for HIV, the device can be used to test for Malaria with a different set of reagents and reference scale. The corresponding color references can be updated, and the numerical scale and the marking can be changed through printing, since the colors, analyte and the numerical scale are printed on paper. The electronic layout remains the same.

Figure 14:
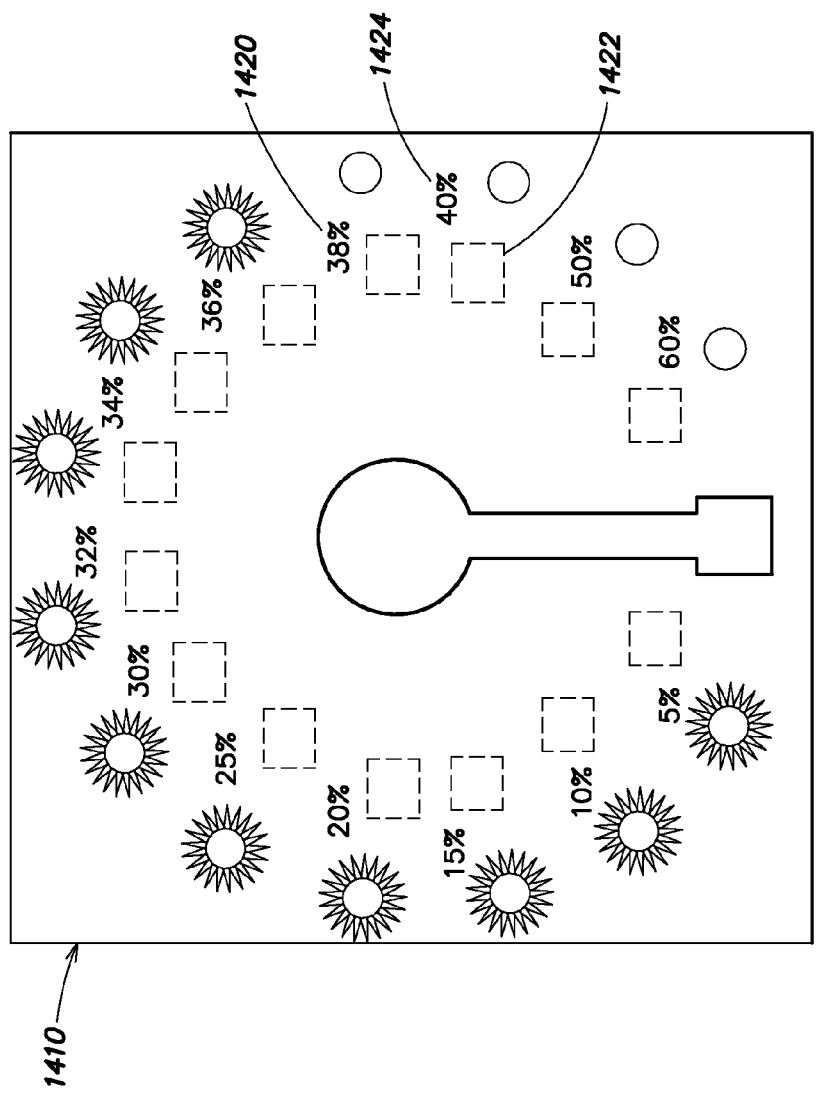
FIG. 14 illustrates a circular indicator having a non-linear scale, according to one example.

FIG. 14 illustrates a circular indicator 1410 having a non-linear scale. Each of the gradated reference wells 1420, 1422, . . . , serves as a comparison point. There may be any number of wells and comparators. More comparisons enable a higher resolution. In addition, the scale does not have to be uniform. In other words, the gradation does not necessarily have to increase linearly. The gradation may show a higher resolution in the range where the diagnosis requires more sensitivity, such as where the sample concentration more likely will fall in. In one example, in the middle of the range the resolution is higher.

In the example illustrated in FIG. 14, the resolution is initially at 5%, and is at 10% at the higher end of the range. From the concentration of 32% to 40%, the resolution is set to be 2%. For example, a reference well has a concentration that is calibrated to ≤38%, and a reference label 1420 of 38% is printed adjacent to it. The next reference well 1422 is calibrated to indicate a concentration of ≤40%, and a reference label 1424 of 40% is printed adjacent to it.

Figure 15:
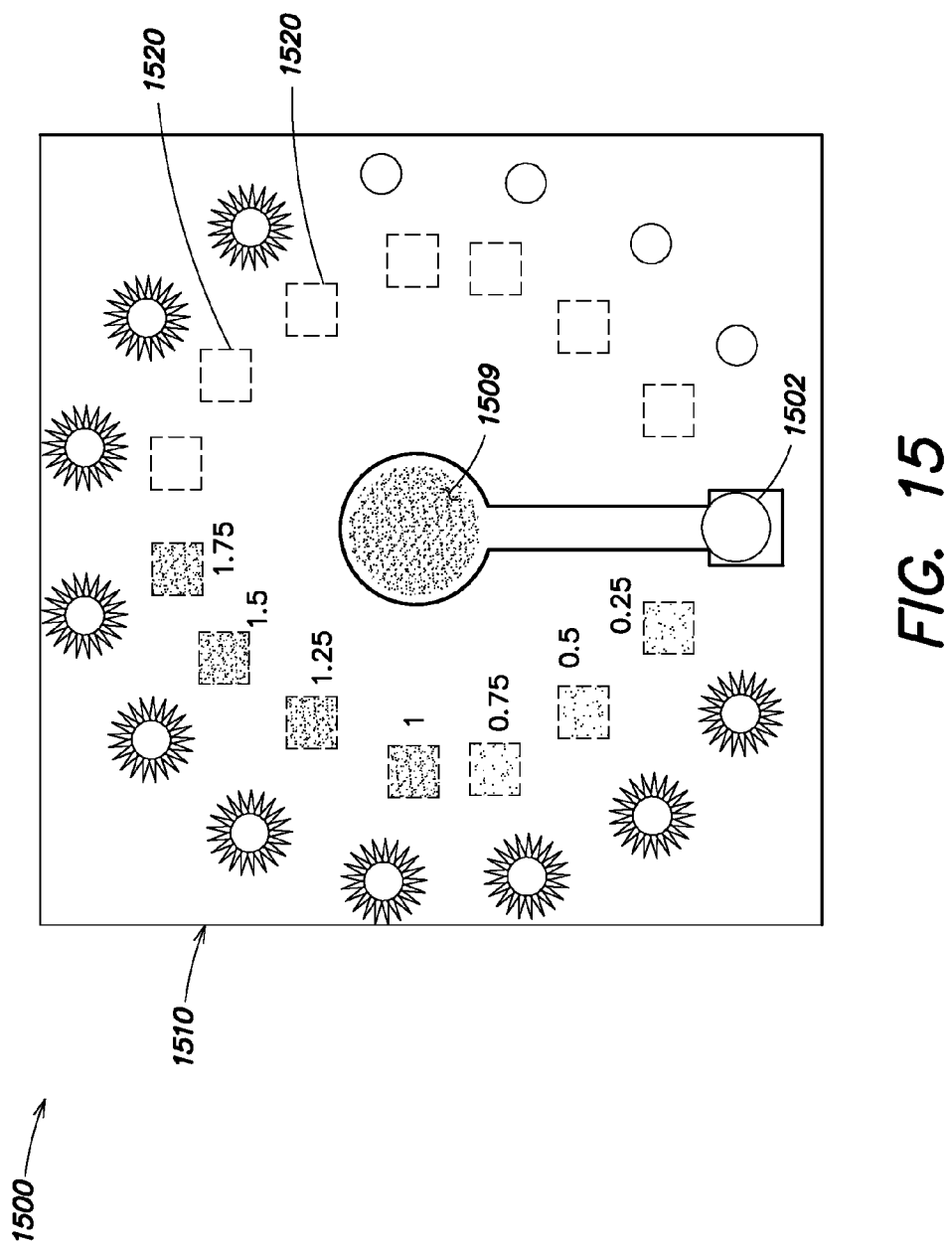
FIG. 15 illustrates an operation of a circular indicator in conjunction with a diagnostic device according to one example.

FIG. 15 illustrates an operation of a circular indicator 1510 in conjunction with a diagnostic device 1500 according to one example. The sample 1502, such as blood, is disposed in the entrance well, and is transferred through the channel, filtered, and/or reacted with a reagent in the sample well to become a derivative 1509 to be analyzed for its concentration of a certain analyte, such as glucose. The color and/or opacity of the derivative can be derived from a photocurrent generated by a photodetector from light transmitted, reflected, or scattered from the sample well. The color and/or opacity can then be compared with those of the reference wells 1520, which have calibrated scales 0.25, 0.5, 0.75, . . . .

Figure 16:
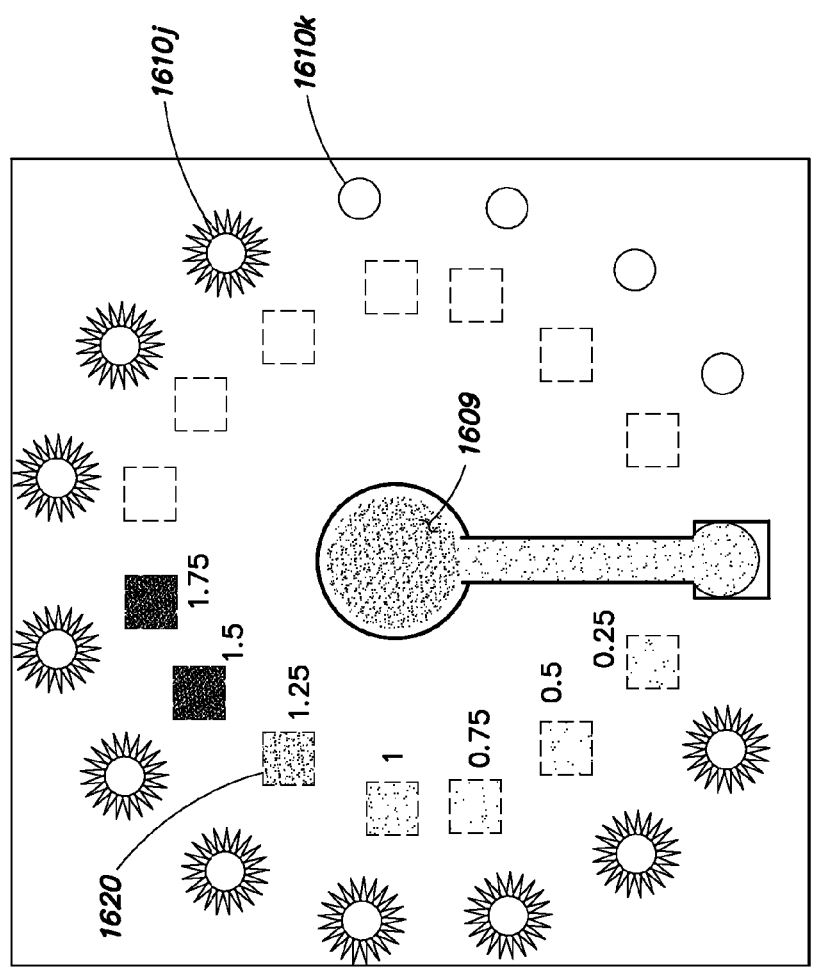
FIG. 16 illustrates another example of operation of a circular indicator in conjunction with a diagnostic device according to one example.

FIG. 16 illustrates another example of operation of a circular indicator in conjunction with a diagnostic device according to one example. As shown, the derivative 1609 from the sample has a color or opacity matching one of the reference dyes 1620 that is calibrated for a concentration of 1.25. LED indicator 1610*j*, which corresponds to the concentration of 1.25, and those LED indicators below, lights up, while its neighboring LED indicator 1610*k* and higher remain unlit. This provides an easy to read indication of the concentration to the user.

Figure 17A:
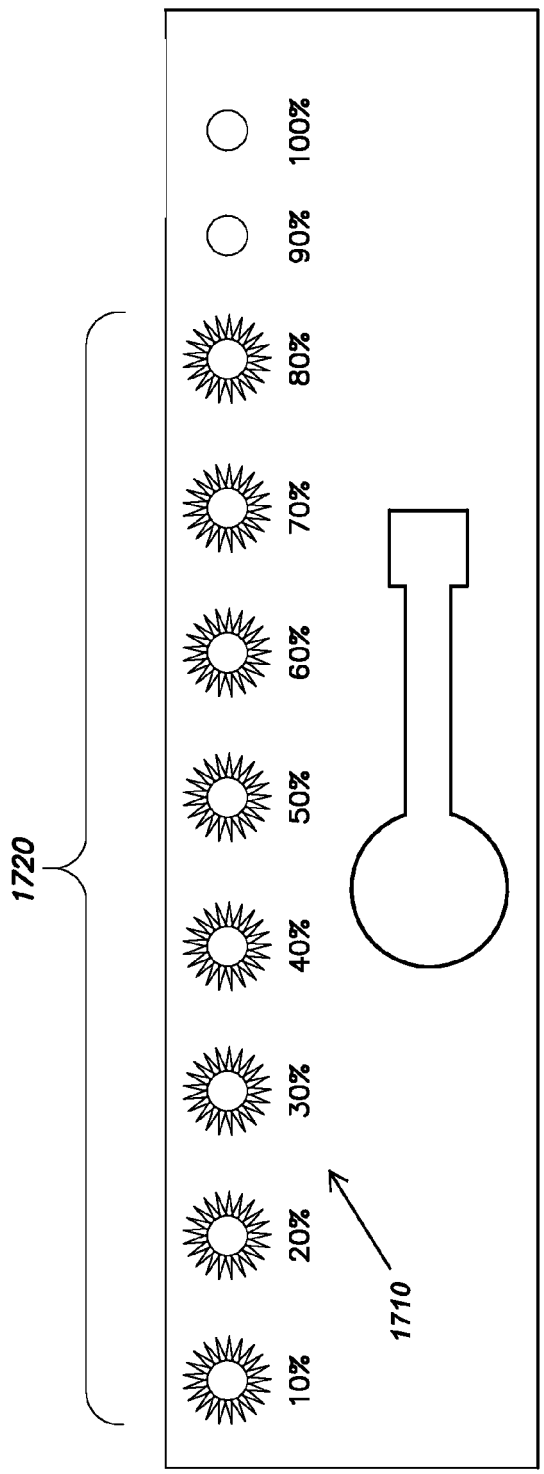
FIG. 17A is a schematic diagram of an indicator having a plurality of indicator LEDs arranged in a substantially linear configuration, according to one example.

Other display methods are possible. For example, FIG. 17A is a schematic diagram of an indicator 1710 having a plurality of indicator LEDs arranged in a substantially linear configuration. The indicator 1710 forms a broken line. The number of LEDs 1720 that light up is proportional to the length of the line that indicates a concentration of the analyte.

Figure 17B:
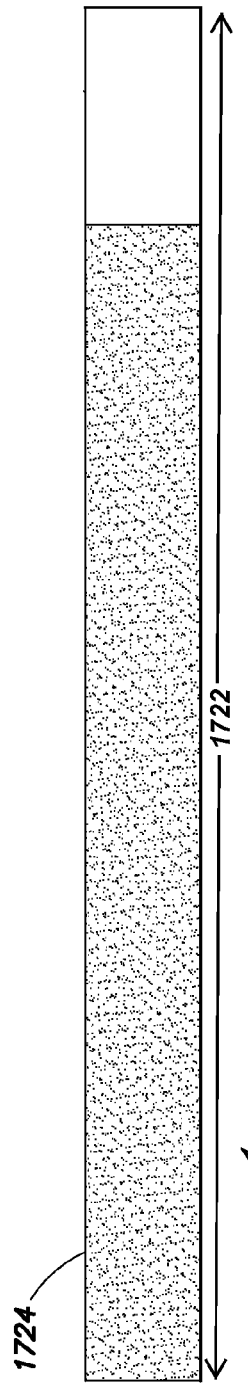
FIG. 17B is a schematic diagram of an indicator based on a band of thermochromic ink, according to one example.

FIG. 17B is a schematic diagram of an indicator 1720 having a band of thermochromic ink 1722 printed on the substrate. A heater (not shown) can be used to heat up a portion of the thermochromic ink 1724, the length of which indicates a concentration of the analyte. The color change of the thermochromic ink 1722 can be continuous as shown in FIG. 17B, or can be non-continuous, such as forming a broken band or line similar to the LED indicator 1710 illustrated in FIG. 17A.

Figure 18:
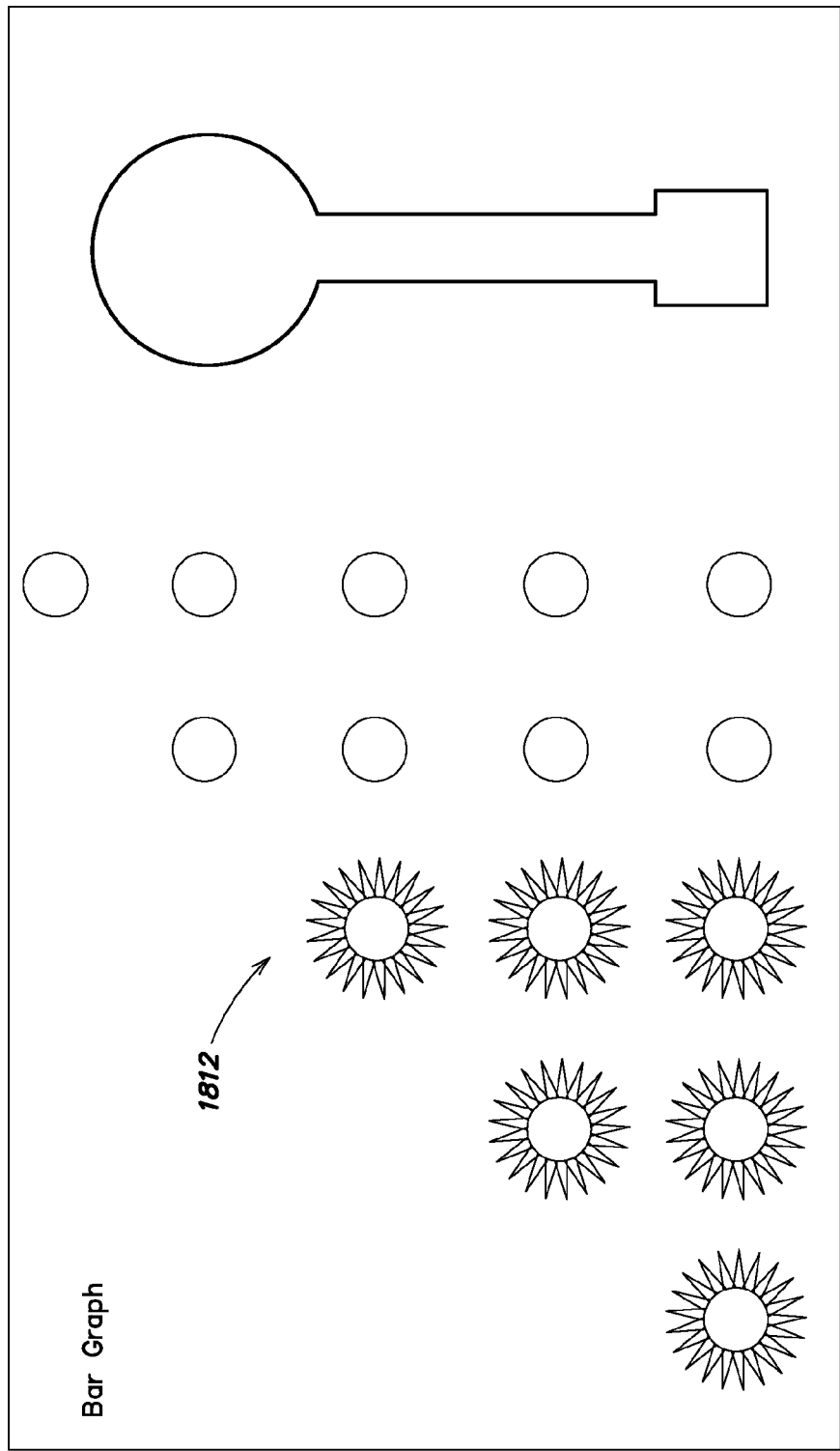
FIG. 18 is a schematic diagram of an indicator having a plurality of indicator LEDs arranged in a bar-shaped configuration, according to one example.

FIG. 18 is a schematic diagram of an indicator 1810 having a plurality of indicator LEDs arranged in a bar-shaped configuration, where the height of the highest bar 1812 that lights up indicates a concentration of the analyte.

Figure 19:
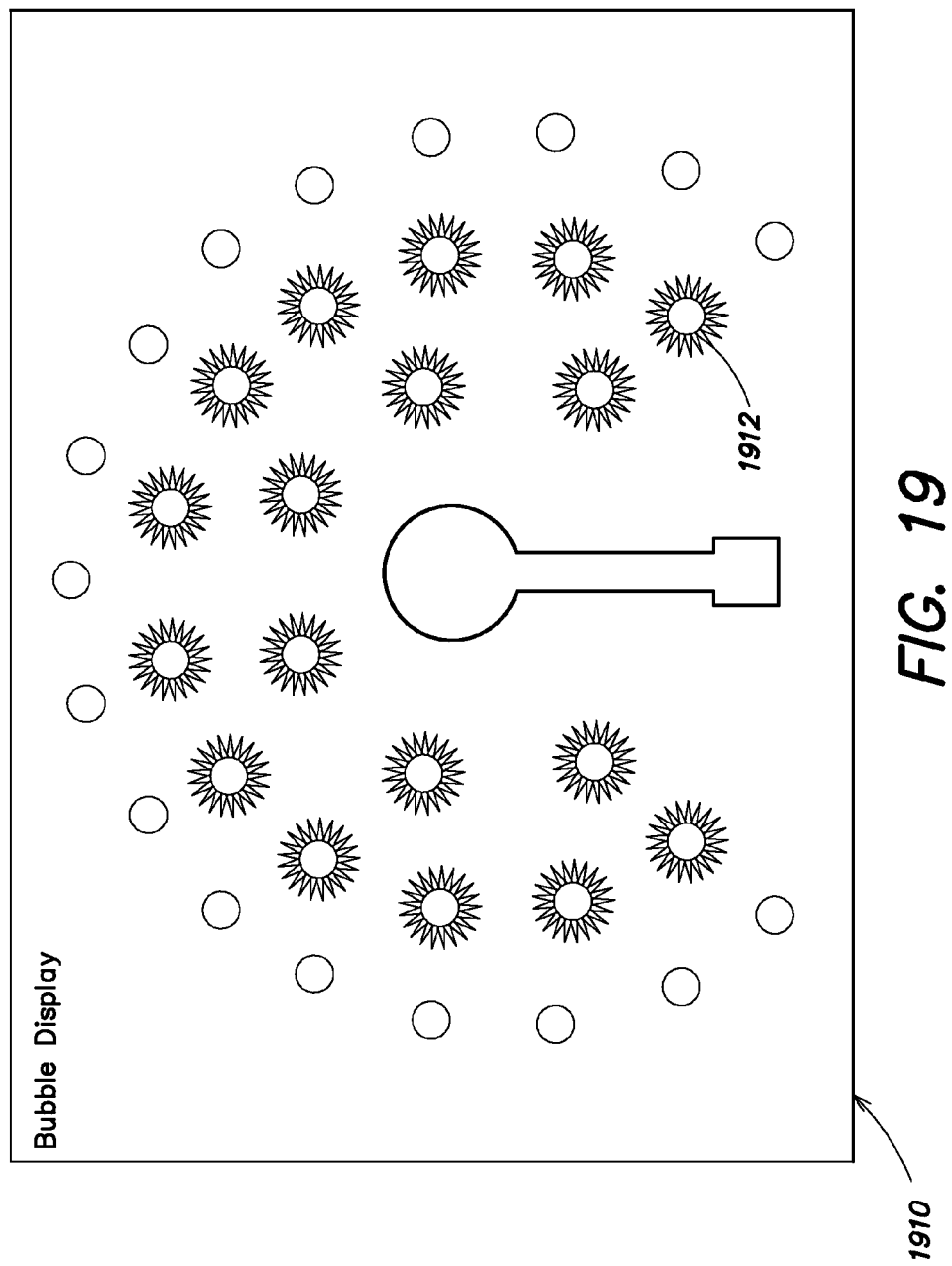
FIG. 19 is a schematic diagram of an indicator having a plurality of indicator LEDs arranged in a bubble display configuration, according to one example.

FIG. 19 is a schematic diagram of an indicator 1910 having a plurality of indicator LEDs arranged in a bubble display configuration, where the radius of the outer most ring 1912 that lights up indicates a concentration of the analyte.

Figure 20A:
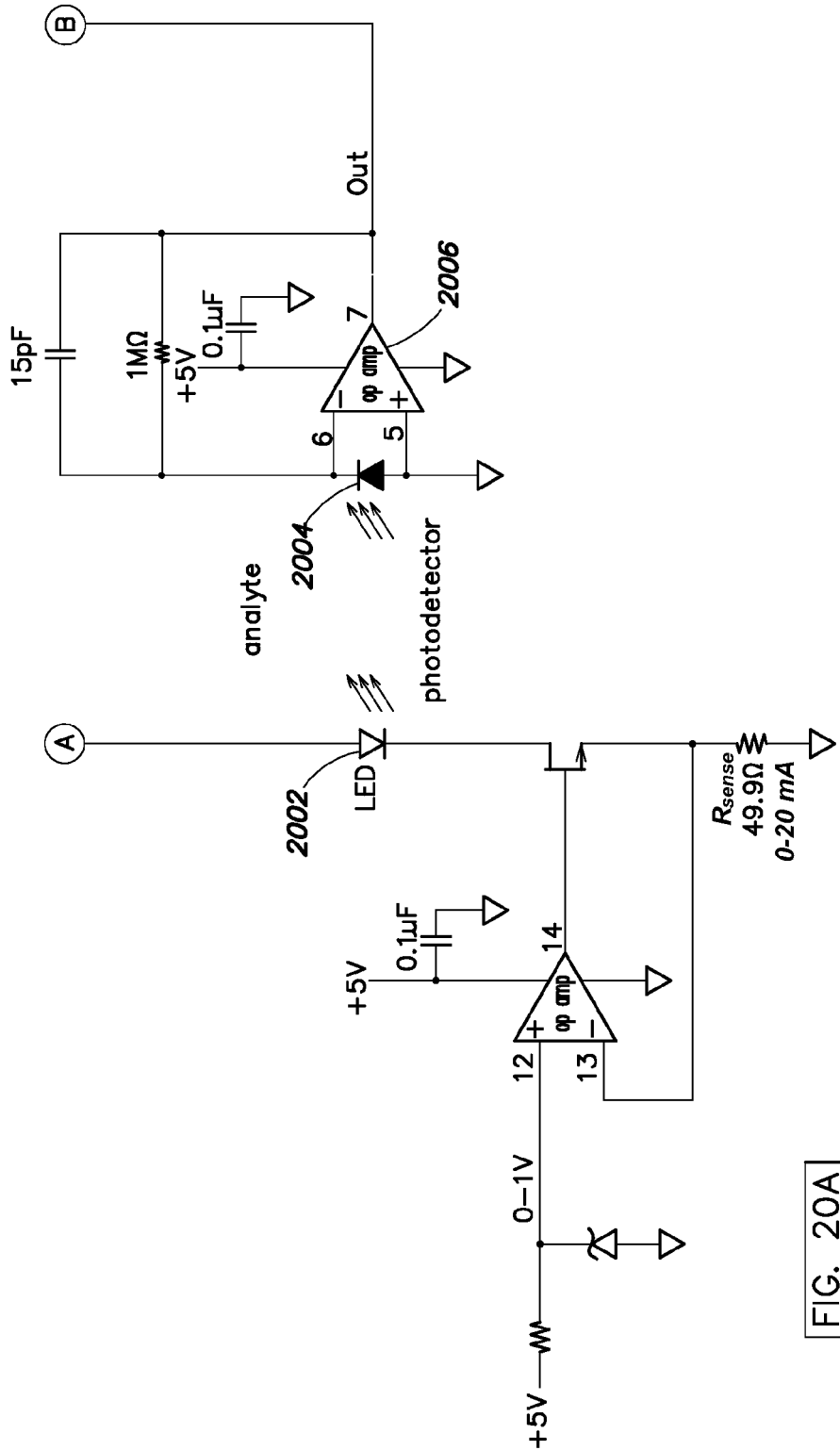
FIGS. 20A and 20B illustrate an electronic circuit diagram of an array of comparators for analyzing photoelectric signals from a device according to one example.
Figure 20B:
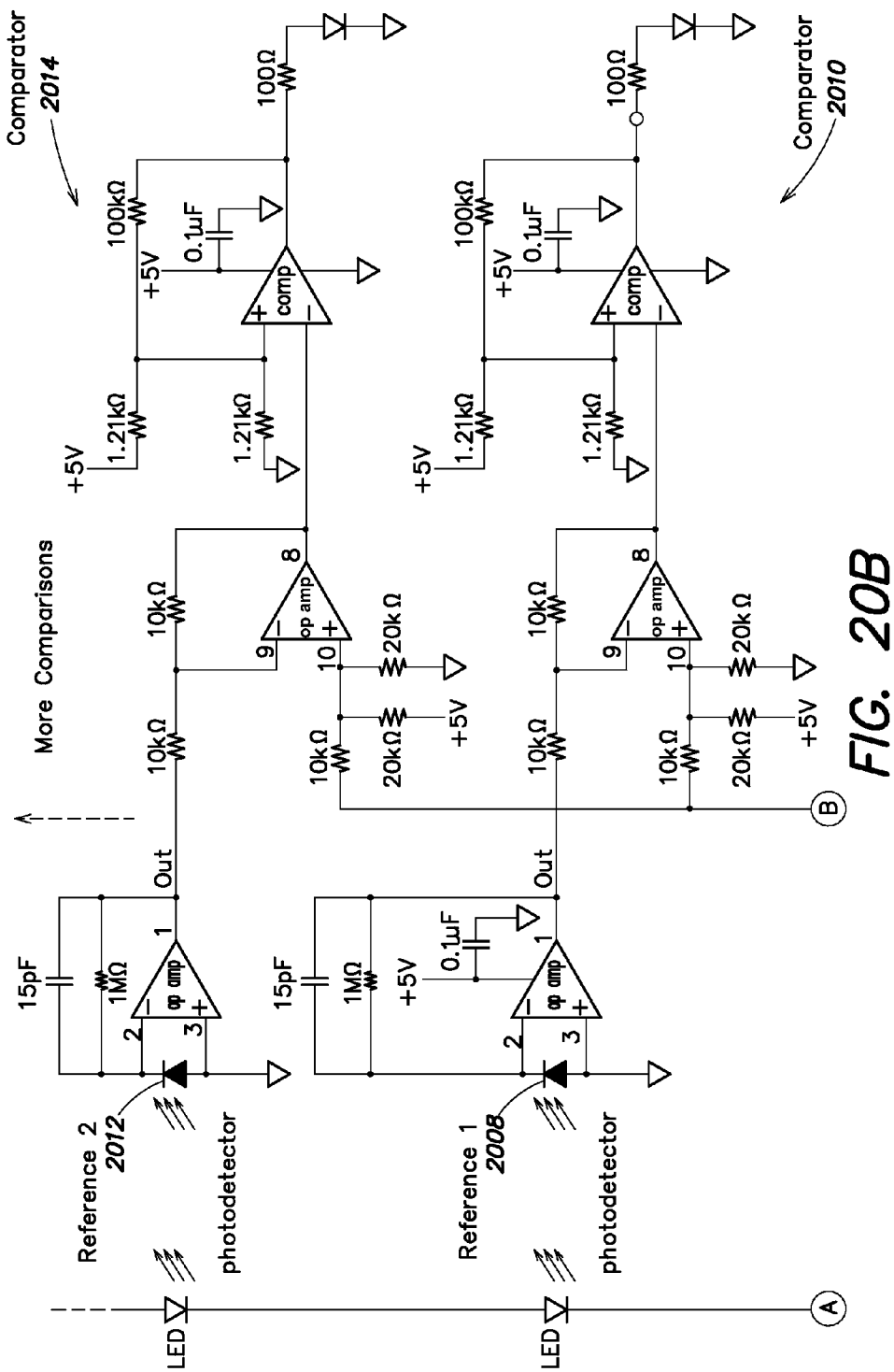

FIGS. 20A and 20B illustrate a circuit diagram of an array of comparators for analyzing photocurrent signals from a device according to one example. As shown the illumination LED 2002 illuminates the sample, the light from which is detected by the sample photodetector 2004. The photocurrent from the photodetector 2004, after being amplified by its associated operational amplifier 2006, is compared with the photocurrent from a first reference photodetector 2008 by a first comparator 2010. The photocurrent from the photodetector 2004, after being amplified by its associated amplifier 2006, is also simultaneously compared with the photocurrent from a second reference photodetector 2012 by a second comparator 2014. Many more references and comparators can be included an electronic circuit based on FIGS. 20A AND 20B.

Example devices herein may provide quantitative information relating to a sample or a derivative of the sample based at least in part on analysis of an electrical signal from the sample or the derivative.

Figure 21:
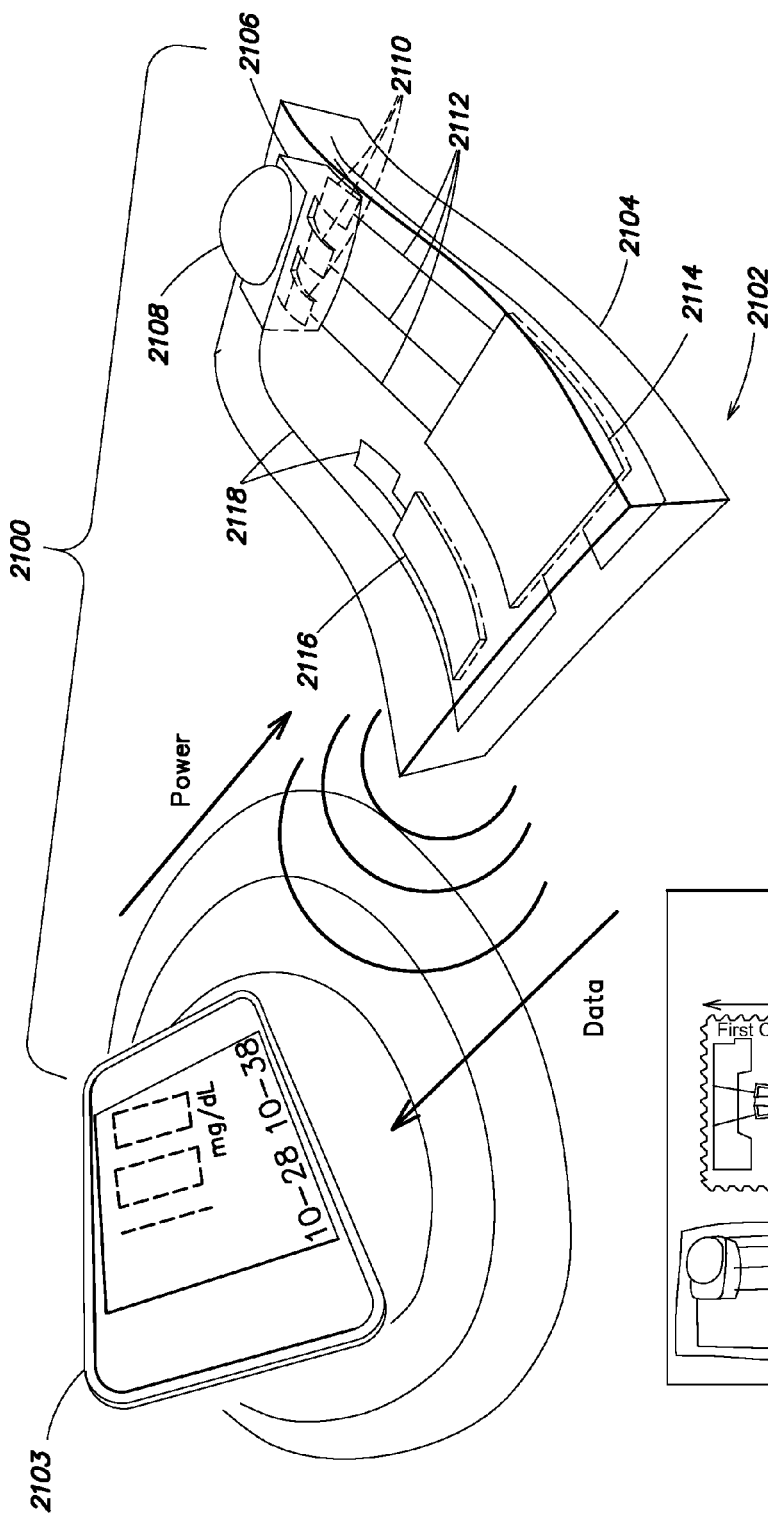
FIG. 21 illustrates a diagnostic system having an RF coupling with an external reader apparatus, according to one example.

FIG. 21 illustrates an example diagnostic system 2100 including a paper-based microfluidic device 2102 having an RF coupling with a reader apparatus 2103. The reader apparatus 2103 can be, for example, a cellular phone or a personal digital assistant (PDA) having a built-in RF inductive coupling function.

The device 2102 is fabricated on a paper substrate 2104, which can be hydrophobic. A portion 2106 of the paper substrate may be hydrophilic, and helps localize a sample (e.g., a drop of whole blood) 2108 to the test region and absorbs the sample 2108 for contact with at least a pair of electrodes.

In one example, the electrodes send a DC current excitation through the sample. In another example, a modulated current is used to excite the sample. An electrode pair can measure impedance of the sample using two or four point measurement method.

In the example shown in FIG. 21, three electrodes 2110 are employed to realize an electrochemical sensing to quantify glucose concentrations in a small amount of plasma (1-10 µL).

The plasma can be filtered from whole blood, for example, during the wicking process through the hydrophilic paper substrate 2106, which can serve as a filter paper. Alternatively, the plasma can be filtered from the blood 2108 and drawn through microfluidic channels (not shown) to the three electrodes where a series of chemical reactions take place. The three electrodes include a working electrode, a counter electrode, and a reference electrode, similar to those used in existing impedance-based glucose readers.

The working electrode is where the electrons are produced. The reference electrode applies a constant voltage (e.g., ~400 mV, with reference to the working electrode) to drive the chemical reactions and induce a measurable current. The counter electrode completes the circuit. That is, the electrochemical signal from the reaction can be detected as the measurable current.

Glucose present in the plasma is converted to gluconic acid by glucose oxidase, precoated in hydrophilic paper substrate 2106 as the reagent. Two electrons are released via an intermediary molecule, $K_3Fe(CN)_6$ and generate electrical current that is proportional to the concentration of glucose in the plasma.

Interconnects 2112 electrically couple the electrodes 2110 with a potentiostatic circuit 2114, which generates an output signal indicating the glucose level in the plasma. The output signal can be displayed onboard the device 2102, for example using the indicator as described above with respect to other examples according to the principles herein. Alternatively, in the example shown in FIG. 21, the output signal can be transmitted by a magnetically-coupled transceiver 2116, through magnetic induction coils or RF antennae 2118, to the reader apparatus 2103.

The reader apparatus 2103 can have more processing power than the onboard electronics of the device 2102. In addition, the reader apparatus 2103 can power the device 2102 through magnetic induction.

Inductive coupling onboard diagnostic device 2102 may provide the benefits of much lower cost than other wireless alternatives (e.g., Bluetooth). Also, since it can scavenge power, the device 2102 does not require the integration of more expensive, inflexible batteries onboard. In addition, the possibility of using cellular phones having inductive coupling and other near field communication modules (i.e., RFID chips) integrated therein open up opportunities for using inductive coupling transceivers, microprocessors, and display drivers onboard the cellular phones to readily communicate with the diagnostic devices wirelessly and display results.

Adequate power levels can be transmitted via the magnetic field when an inductive transmitter coil on the reader apparatus (e.g., the cellular phone) is within 1-3 cm of the device's receiver coil. This power can drive the diagnostic device's circuitry once a drop of blood is captured by the device. In one example, about 94% of the power at 6 volts, 22 mA can be transferred over a relatively short distance of about 1-3 cm at kilohertz and megahertz transmission frequencies. The diagnostic device circuitry can be designed to draw significantly less power (e.g., ~50 µA at 6 Volts DC) for a given measurement.

In one example of the disclosure, data transfer through the transmitter coil of the diagnostic device 2102 can be switched on once blood plasma contacts the electrodes. The reader apparatus 2103 captures data streaming from the device 2102 when they are within a communication range, e.g., <3 cm. In this example, the diagnostic device has the built-in inductor coils and passive components, while active components such as the microprocessor, the display driver, and memory are part of the reader apparatus 2103.

Alternatively, these active components can be integrated in the diagnostic device 2102, for example using the silicon printing techniques described in the present application. In yet another example, rigid microprocessing units can be included onboard the paper substrate and coupled to flexible electrodes and antenna.

The inset of FIG. 21 shows that the flexible device 2102 can be fabricated to have a size comparable to a postage stamp, i.e., about 2.2 cm×2 cm.

The entire measurement cycle may take approximately 10 seconds for the diagnostic device to complete a diagnosis, starting from once a drop of blood contacts the electrodes.

The onboard circuitry can then be used to record the electrical current continuously and output a single current value as a diagnostic criterion. Since the current undergoes an initial transient peak and then approaches a steady state, the current value can vary depending on the specific time selected for outputting the single current value.

In accordance with one example of the disclosure, all of the diagnostic devices will be configured to capture the electrical current value at the same time (typically following the transient peak at about 3 seconds). The current measured at this time represents the output measurement of the integrated microfluidic diagnostic device, which can be compared to a current vs. glucose calibration curve to determine the glucose concentration. The raw current data can be transferred wirelessly as an analog signal, or digitized onboard the diagnostic device. The electronic circuits along with passive components (resistors, capacitors) on the diagnostic device filter out high frequency noise, e.g., through a synchronous demodulation, and optimizes the signal prior to wirelessly transferring the data to a remote unit.

Figure 22:
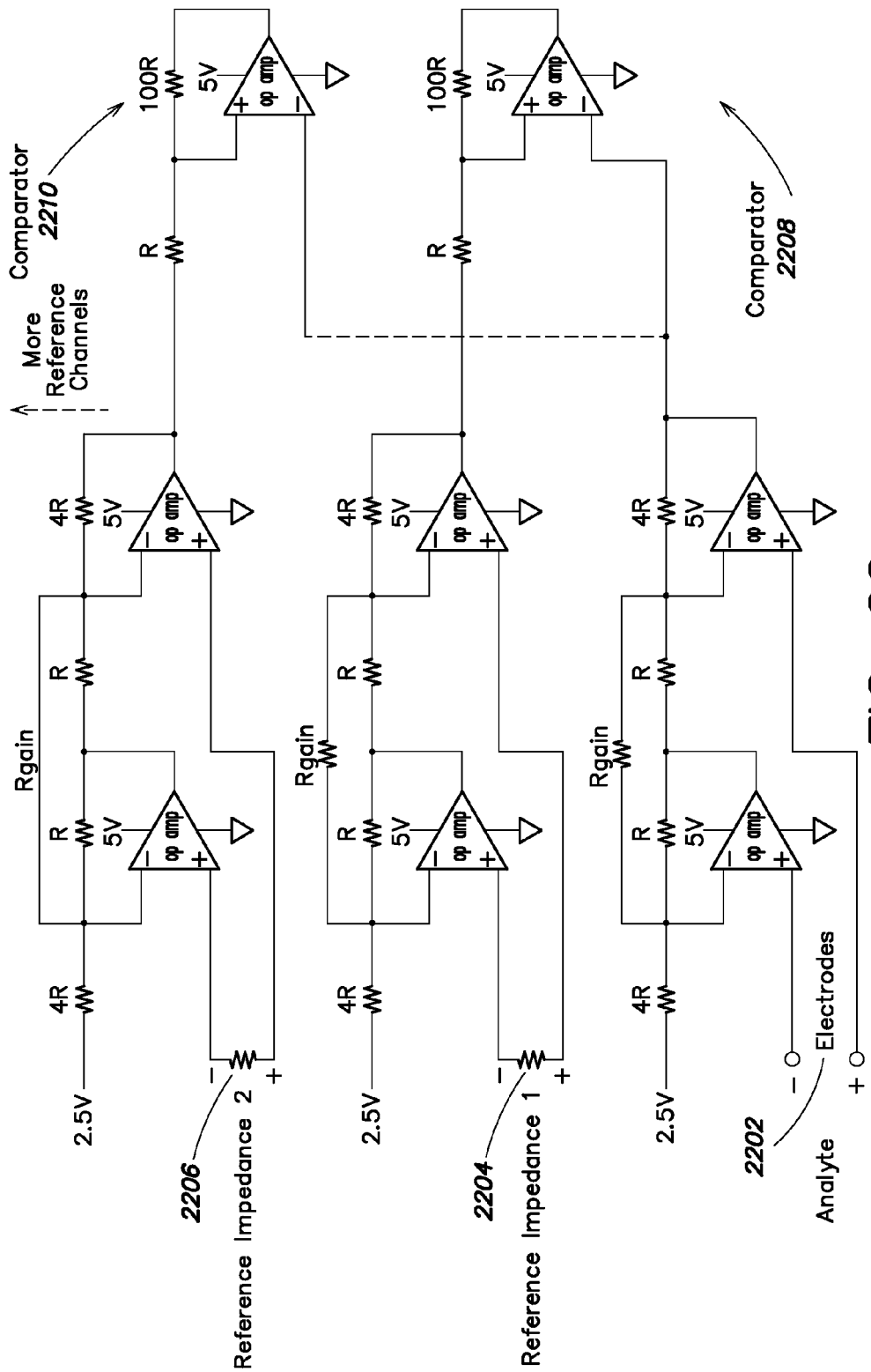
FIG. 22 illustrates a circuit diagram of an array of comparators for analyzing impedance signals from a device according to one example.

FIG. 22 illustrates a diagram of an example circuit of an array of comparators for analyzing impedance signals from a device according to one example. As shown, the impedance is measured by a pair of electrodes 2202. A plurality of reference impedances 2204, 2206 are included onboard the device. The output signal from the pair of electrodes 2202 is compared with the reference signals from the reference impedances 2204, 2206, respectively, with first and second comparators 2208, 2210. Many more reference channels and comparators can be included in the device to achieve the desired measurement resolution.

Figure 23A:
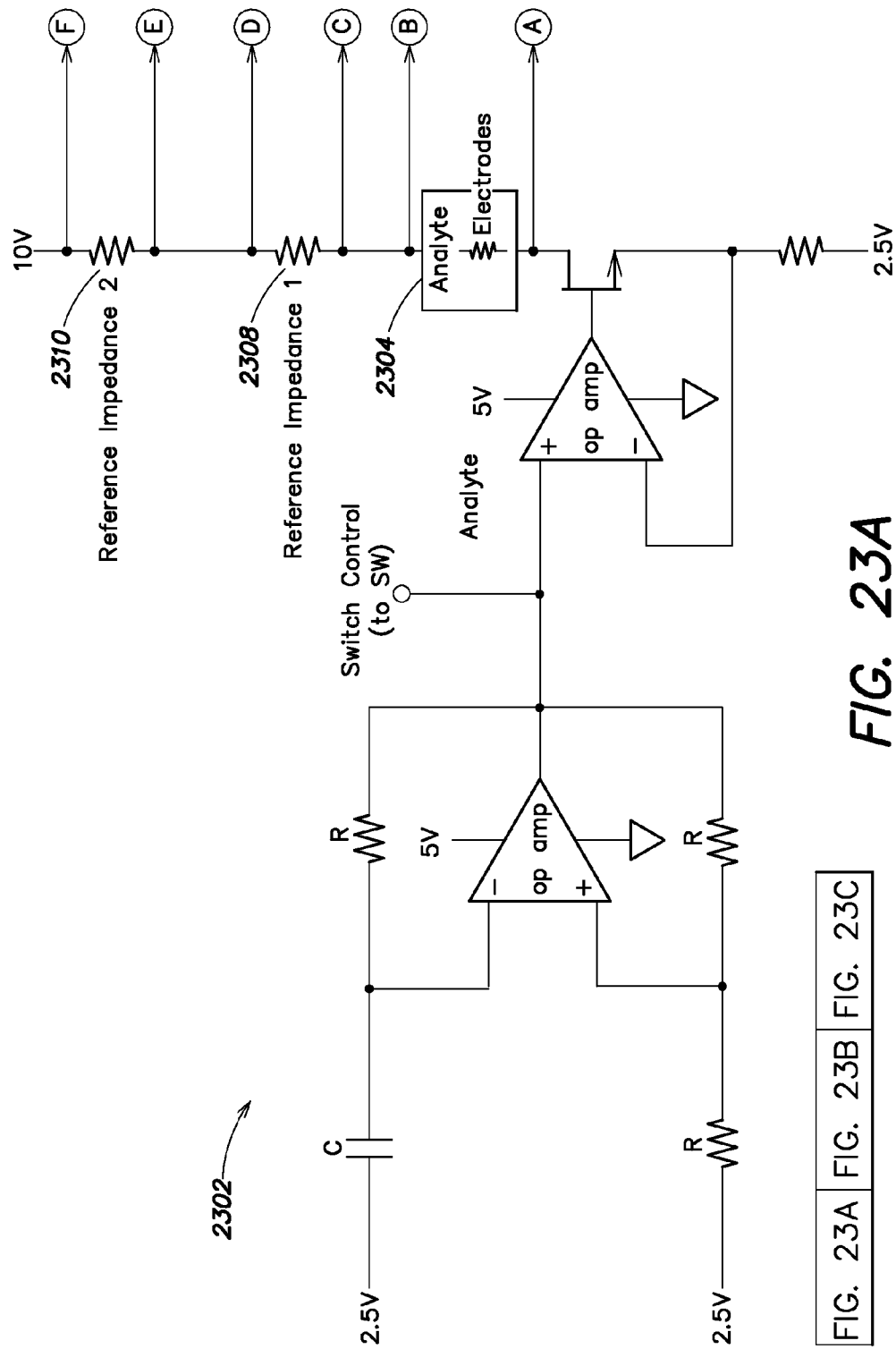
FIGS. 23A, 23B and 23C illustrate a diagram of a circuit having a synchronous demodulation for analyzing impedance signals from a device according to one example.
Figure 23B:
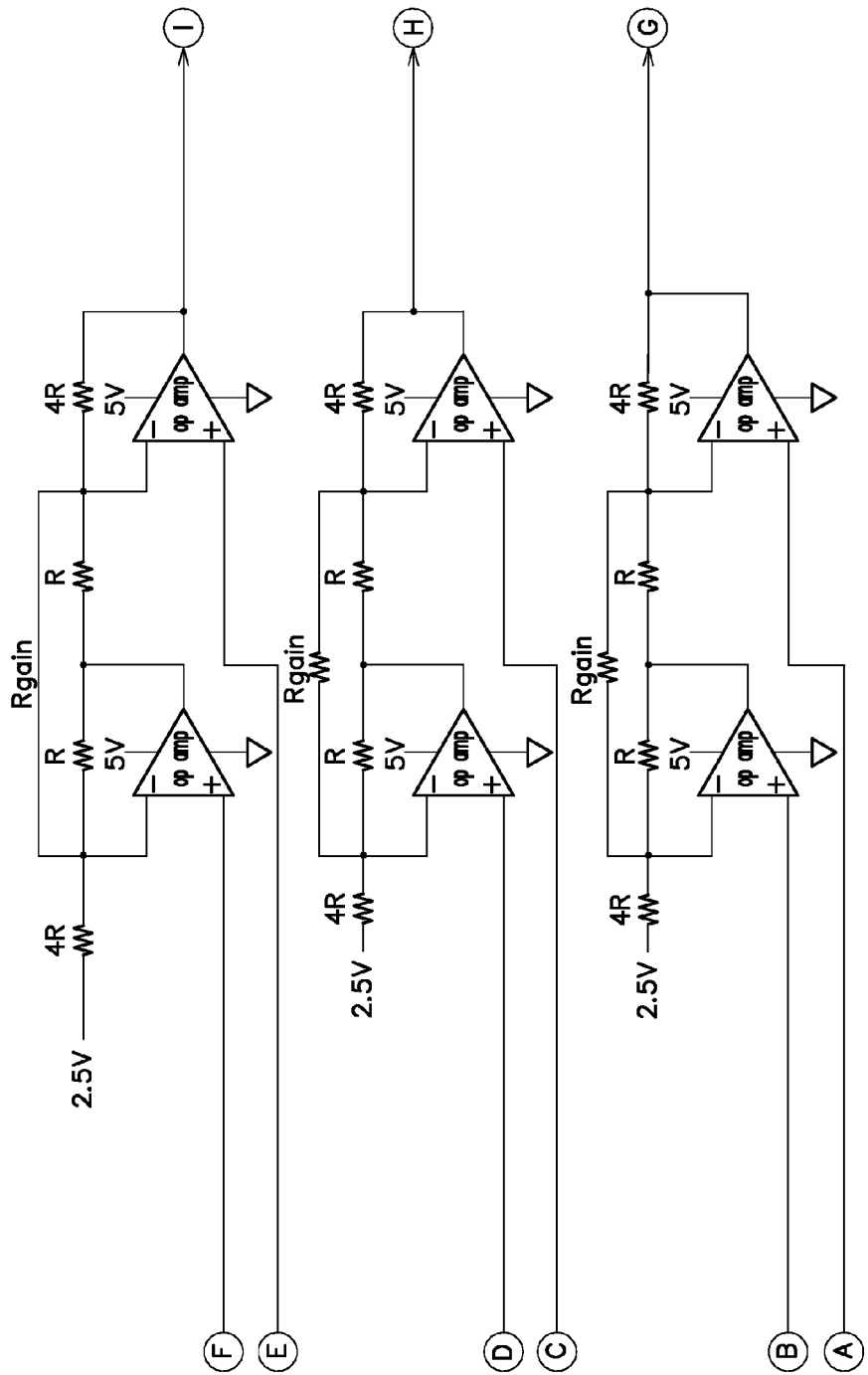
Figure 23C:
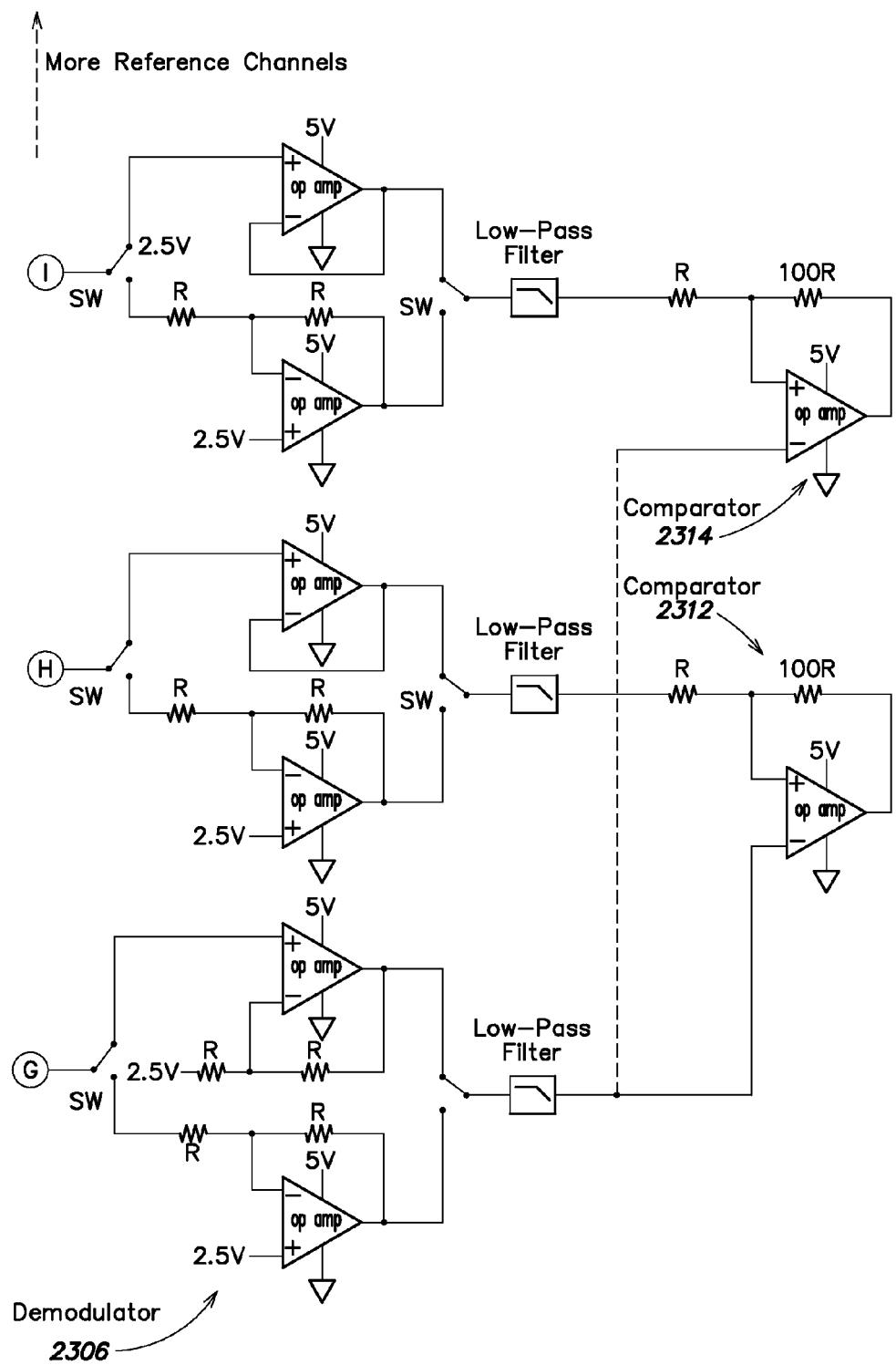

FIGS. 23A, 23B and 23C illustrate a diagram of an example circuit having a synchronous demodulation for analyzing impedance signals from a device according to one example. A modulation circuit 2302 modulates an electrical input signal to the sample 2304 at a given frequency. The output impedance signal from the sample 2304, after being amplified, is demodulated with a demodulator 2306 at the same frequency of the modulation circuit 2302. The demodulated signal is compared with reference signals from reference impedances 2308, 2310, respectively, using comparators 2312, 2314. The synchronous demodulation process rejects noise current, and is equivalent to the color filter used in the diagnostic device based on optical signals as illustrated in FIG. 12.

Additional analysis techniques can be adopted in the device based on impedance measurements. For example, a spectrum of impedance can be captured by sweeping the frequency during excitation of the sample. Impedance is measured at gradated frequencies. Information is obtained for various frequencies much like an fast Fourier transform (FFT).

In accordance with some examples, three dimensional (3-D) devices are provided. These devices may have electronic components/electrodes embedded within its layers. They may be formed from patterned paper and double-sided adhesive tapes. Three dimensional devices can distribute fluid in a single layer of paper and between adjacent stacks. Three dimensional paper devices can be assembled in large manufacturing scales affordably by stacking large sheets of patterned paper and tape and by cutting the stacks into many individual devices. Multi-layered microfluidic designs provide the devices with the ability to filter blood (e.g., separating plasma) and cause multiplex movements of small amounts of plasma into different test zones.

In one example, three-dimensional paper-based microfluidics may improve accuracy through redundant testing of the glucose level in a particular fluid sample. Moreover, holes patterned in paper and tape (filled with cellulose powder) suggests that multiple independent blood samples (denoted by different colored dyes) can be tested independently. Using this configuration of test zones separated by hydrophobic regions (of wax and/or photoresist), multiple tests on a single device can be achieved by integrating multiple electrode pairs with the holes. Potentiostatic circuitry can be designed to support distinct sets of electrodes associated with a number of different test zones.

Figure 24:
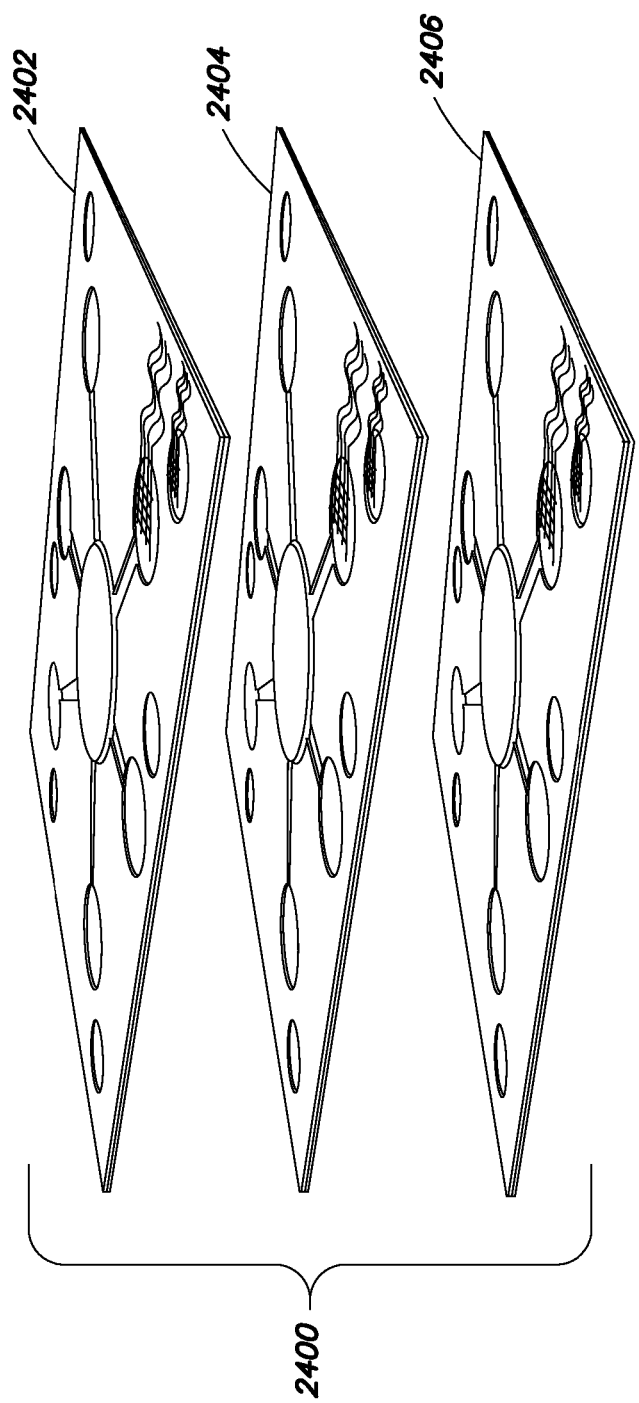
FIG. 24 is a perspective view of a 3-D device including a stack of substrates to perform a plurality of measurements thereon, according to one example.

FIG. 24 is a perspective view of a 3-D device 2400 including a stack of substrates 2402, 2404, 2406 to perform a plurality of measurements thereon, according to one example. Each layer of the stack can include a substantially complete device similar to the device 300 illustrated in FIG. 3, or the device 400 illustrated in FIG. 4. In one example, at least two substrates of the plurality of substrates 2402, 2404, 2406, . . . are configured to perform a redundant measurement to reduce erroneous diagnosis. In some other examples, different layers in the stack perform different measurements, on a same sample or different samples, in parallel.

Figure 25:
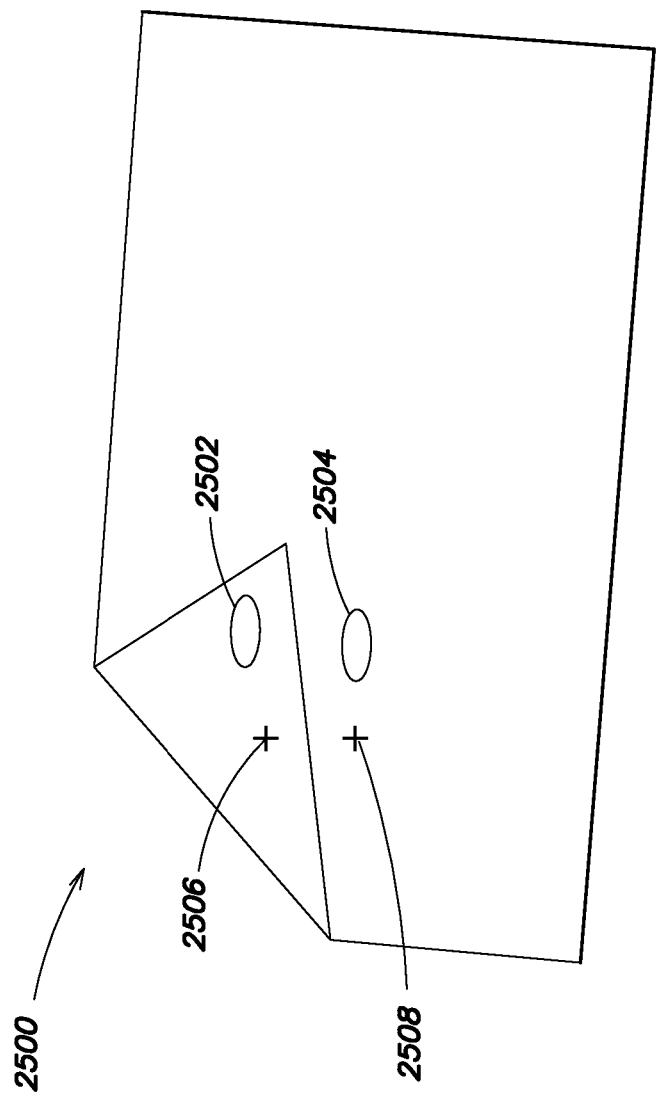
FIG. 25 is a schematic diagram of a foldable device having a 3-D structure formed by folding 2-D substrate, according to one example.

FIG. 25 is a schematic diagram of a foldable device 2500, which can be similar to the device 300 illustrated in FIG. 3, or the device 400 illustrated in FIG. 4. The ability of folding the lab-on-the-paper allows the making of a 3-D device 2500 from a 2-D substrate. The 2-D substrate can be folded multiple times to form a complex 3-D structure.

In one example, at least two components 2502, 2504 of the device are configured to be aligned by folding the substrate. The two components can be two electrical contacts for example, and the two electrical contacts are configured to form an electrical connection by folding the substrate. The electrical connection, when formed, is configured to power up the device by closing the loop on a circuit. This can be useful, for example, in applications such as meat packing, where when meat is packed, a diagnostic device is folded and powered on, and continues to monitor and indicate the bacterial level in the meat pack.

A plurality of alignment marks or notches 2506, 2508 can be formed in the substrate to aid the alignment process.

In some examples, the components to be aligned through the folding include the sample wells having the samples to be measured, and reagents. For example, a plurality of samples can be disposed in an array at one end of the paper, while an array of reagents integrally formed with the substrate are disposed at the other end of the paper, and reactions can occur when the paper is folded to align the two arrays and contacts are made between the samples and the reagents.

In some other examples, the folding aligns the sample well with the photodetector, both components printed on the same 2-D lateral surface of the substrate. One or more microfluidic channels can be created by placing a water resistant material, such as an elastomer, on either side of the paper. The electronic circuits can be printed on the elastomer on a single side. The photodetector can be disposed on one end of the substrate. The sample well can be disposed on the other end of the substrate on the same side, and can have the sample and an illumination LED disposed therein. When the elastomer is folded, it forms a mechanical structure where light from the LED shines into the photodetector.

The substrate can be easily folded in areas where stretchable/flexible interconnects are disposed. The device 2500 can also be folded across active devices (e.g., LEDs) if they are monolithically fabricated, or have a thickness similar to that of a paper. This folding can be performed manually or automatically with a machine, and alignment may be aided by the/alignment marks printed on the paper.

By using patterned paper as a substrate for the diagnostic devices, a high level of complexity normally only found in much more expensive plastic-based microfluidic systems can be achieved. Additionally, silicon (used for the flexible electronics) is inexpensive, for example, at high manufacturing volumes.

With onboard, flexible circuitry and the natural capillary forces of paper, the devices according to examples of the disclosure can be standalone devices independent of any external equipment, can have a high accuracy resulting from the quantification/calibration, yet are of low cost and can be easily disposable. In contrast, plastic-based microfluidic devices require external pumps, and often require dedicated reader apparatuses. Existing lab-based ELISA tests also need external readers for quantification. These external reader apparatuses are often complex and expensive.

Using flexible electronics on paper substrates also provides the devices with a rugged form factor. The microfluidic patterned-paper platform also makes the devices small and highly portable. These characteristics are beneficial for extending health monitoring and POC services to remote areas. The performance of these circuits can approach that of existing silicon-based electronics, but without degradation upon bending, folding, or twisting.

Since paper can wick by its inherent capillary action, no pump may be needed. The on-board electronics consumes little power, and can be powered by a low-cost, disposable battery.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy disks, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology described above. The computer readable medium or media can be transportable, such that the program or programs stored thereon can be loaded onto one or more different computers or other processors to implement various aspects of the present technology as described above.

The terms "program" or "software" are used herein in a generic sense to refer to any type of computer code or set of computer-executable instructions that can be employed to program a computer or other processor to implement various aspects of the present technology as described above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for providing quantitative information relating to a sample, the device comprising:
  a substrate comprising at least one paper-based portion;
  a sample receiver to receive the sample, wherein the sample receiver is at least partially formed in or disposed on the at least one paper-based portion;
  electronic circuitry at least partially formed in or disposed on the substrate, wherein the electronic circuitry generates at least one analysis result based on an output signal from the sample or a derivative of the sample;
  at least one indicator at least partially formed in or disposed on the substrate, and electrically coupled to the electronic circuitry, wherein the at least one indicator provides an indication of the quantitative information relating to the sample based at least in part on the at least one analysis result; and
  a container at least partially formed in or disposed on the substrate, wherein the container is coupled to the sample receiver to retain the sample or the derivative of the sample.

2. The device of claim 1, wherein the electronic circuitry analyzes the output signal from the sample or the derivative of the sample, and wherein the electronic circuitry generates the at least one analysis result based on the analysis of the output signal.

3. The device of claim 1, further comprising a channel disposed between the sample receiver and the container, and formed at least partially in or disposed on at least one paper-based portion, to transfer the sample or the derivative of the sample from the sample receiver to the container.

4. The device of claim 3, wherein the channel is formed in at least one paper-based portion of the substrate, and wherein at least one paper-based portion is configured to wick the sample or the derivative of the sample from the sample receiver to the container by capillary action.

5. The device of claim 1, further comprising a reagent disposed in the container to react with the sample or the derivative of the sample, when either is present, wherein the output signal comprises a reaction output of the reagent and the sample or the derivative of the sample.

6. The device of claim 5, wherein the substrate further comprises a water resistant material,
  wherein a fluidic channel is formed between at least one paper-based portion and the water resistant material to transfer the sample or the derivative of the sample to the container to react with the reagent.

7. The device of claim 6, wherein the water resistant material comprises (poly)dimethylsiloxane.

8. The device of claim 1, further comprising a reagent disposed in the container to react with the sample or the derivative of the sample, when either is present, wherein the output signal represents a degree to which the reagent reacts with the sample or the derivative of the sample, and wherein the output signal comprises at least one of:
  an optical signal representing the degree to which the reagent reacts with the sample or the derivative of the sample;
  an electrochemical signal representing the degree to which the reagent reacts with the sample or the derivative of the sample;
  an electrical signal representing the degree to which the reagent reacts with the sample or the derivative of the sample; and
  an acoustic signal representing the degree to which the reagent reacts with the sample or the derivative of the sample.

9. The device of claim 8, wherein the optical signal is a color change, wherein the electrical signal is an impedance change, and wherein the acoustic signal is a pressure change.

10. The device of claim 9, wherein the output signal comprises an electrical signal, wherein the electrical signal is an impedance change representing the degree to which the reagent reacts with the sample or the derivative of the sample, and wherein the electrical circuitry comprises at least one pair of electrodes to generate the electrical signal representing the impedance change.

11. The device of claim 10, wherein the sample comprises blood, and wherein:
  the device is configured to filter plasma from the blood;
  the reagent comprises a glucose oxidase to react with glucose in the plasma to form gluconic acid; and the electrical signal provides an indication of a concentration of glucose in the plasma.

12. The device of claim 1, wherein the quantitative information comprises at least one of:
- a glucose level;
- a T-cell concentration;
- a microorganism concentration;
- a water-based pathogen concentration;
- a bovine serum albumin (BVA) concentration;
- a bacterial concentration;
- a viral load;
- an antigen level;
- an antibody level;
- a diagnosis of tuberculosis;
- a diagnosis of dengue fever;
- a cardiac enzyme concentration; and
- a diagnosis of malaria.

* * * * *